(12) United States Patent
Manabe et al.

(10) Patent No.: US 11,071,659 B2
(45) Date of Patent: Jul. 27, 2021

(54) UNDERPANTS-STYLE DISPOSABLE DIAPER AND MANUFACTURING METHOD THEREFOR

(71) Applicant: Daio Paper Corporation, Ehime (JP)

(72) Inventors: Sadanao Manabe, Tokyo (JP); Shuichi Ito, Tokyo (JP)

(73) Assignee: Daio Paper Corporation, Ehime (JP)

( * ) Notice: Subject to any disclaimer, the term of this patent is extended or adjusted under 35 U.S.C. 154(b) by 436 days.

(21) Appl. No.: 16/070,102

(22) PCT Filed: Jan. 17, 2017

(86) PCT No.: PCT/JP2017/001325
§ 371 (c)(1),
(2) Date: Jul. 13, 2018

(87) PCT Pub. No.: WO2017/130782
PCT Pub. Date: Aug. 3, 2017

(65) Prior Publication Data
US 2019/0029896 A1     Jan. 31, 2019

(30) Foreign Application Priority Data
Jan. 28, 2016  (JP) .............................. JP2016-014881

(51) Int. Cl.
*A61F 13/496*      (2006.01)
*A61F 13/84*       (2006.01)
(Continued)

(52) U.S. Cl.
CPC .... *A61F 13/4963* (2013.01); *A61F 13/15593* (2013.01); *A61F 13/15723* (2013.01);
(Continued)

(58) Field of Classification Search
CPC ............ A61F 13/49011; A61F 13/4902; A61F 13/496; A61F 13/4963; A61F 13/51496; A61F 2013/49042; A61F 2013/8497
See application file for complete search history.

(56) References Cited

U.S. PATENT DOCUMENTS 7,530,972 B2 * 5/2009 Ando ................ A61F 13/15593
604/385.27
8,672,915 B2 * 3/2014 Kuwano ............... A61F 13/496
604/392
(Continued)

FOREIGN PATENT DOCUMENTS

EP           3053558       8/2016
JP          2004254861     9/2004
(Continued)

OTHER PUBLICATIONS

Extended European Search Report for EP 17744013.8 dated Aug. 26, 2019.
(Continued)

*Primary Examiner* — Catharine L Anderson
(74) *Attorney, Agent, or Firm* — Andrus Intellectual Property Law, LLP

(57) ABSTRACT

A method of producing an underpants-type disposable diaper includes forming an outer member having a non-stretchable region disposed in an intermediate region in the width direction and stretchable regions disposed on the two sides of the non-stretchable region in the width direction by: fixing elastic members to an inner sheet layer and an outer sheet layer in at least two edge portions of portions to be the stretchable regions without fixing the elastic members to the inner sheet layer nor the outer sheet layer in a portion to be the non-stretchable region; disposing a graphic sheet and disposing a no-extra-sheet region between the inner sheet layer and the outer sheet layer in the side portion of the
(Continued)

non-stretchable region; cutting the elastic members and leaving cut marks and idle elastic members over the no-extra-sheet region; and leaving the elastic members in a region overlapping with the graphic sheet uncut.

18 Claims, 16 Drawing Sheets

(51) Int. Cl.
  *A61F 13/49* (2006.01)
  *A61F 13/15* (2006.01)
  *B29D 99/00* (2010.01)
(52) U.S. Cl.
  CPC .... *A61F 13/15739* (2013.01); *A61F 13/4902* (2013.01); *A61F 13/496* (2013.01); *A61F 13/49011* (2013.01); *A61F 13/84* (2013.01); *A61F 2013/49042* (2013.01); *A61F 2013/49093* (2013.01); *A61F 2013/8497* (2013.01); *B29D 99/0064* (2013.01)

(56) References Cited

U.S. PATENT DOCUMENTS

| | | | |
|---|---|---|---|
| 9,028,461 B2 * | 5/2015 | Kobayashi | A61F 13/49012 604/385.3 |
| 9,233,031 B2 * | 1/2016 | Ichihara | A61F 13/51496 |
| 9,895,276 B2 * | 2/2018 | Mizobuchi | A61F 13/4963 |
| 10,413,453 B2 * | 9/2019 | Adachi | A61F 13/15593 |
| 10,537,482 B2 * | 1/2020 | Fukasawa | A61F 13/49011 |
| 2004/0230171 A1 | 11/2004 | Ando et al. | |
| 2012/0095429 A1 | 4/2012 | Kobayashi et al. | |
| 2016/0206481 A1 | 7/2016 | Adachi et al. | |

FOREIGN PATENT DOCUMENTS

| | | | |
|---|---|---|---|
| JP | 2004298362 | 10/2004 | |
| JP | 2010158590 | 7/2010 | |
| JP | 201136538 | 2/2011 | |
| JP | 2012100694 | 5/2012 | |
| JP | 2013176453 | 9/2013 | |
| JP | 201591304 | 5/2015 | |
| WO | 2014192982 | 12/2014 | |
| WO | 2015046338 | 4/2015 | |
| WO | WO-2015146245 A1 * | 10/2015 | A61F 13/4902 |

OTHER PUBLICATIONS

International Search Report, PCT/JP2017/001325, dated Apr. 11, 2017.

* cited by examiner

UNDERPANTS-STYLE DISPOSABLE DIAPER AND MANUFACTURING METHOD THEREFOR

CROSS-REFERENCE TO RELATED APPLICATIONS

This application is the U.S. national stage application of International Application PCT/JP2017/001325, filed Jan. 17, 2017, which international application was published on Aug. 3, 2017, as International Publication WO 2017/130782 in the Japanese language. The International Application claims priority of Japanese Patent Application No. 2016-014881, filed Jan. 28, 2016. The international application and Japanese application are both incorporated herein by reference, in entirety.

TECHNICAL FIELD

The present invention relates to an underpants-type disposable diaper including a graphic sheet on which designs are printed and a method of producing the diaper.

BACKGROUND ART

A typical underpants-type disposable diaper includes an outer member disposed in a front body and a back body provided as a single segment or two discrete segments and an inner member disposed from the front body to the back body adjacent to the inner face of the outer member and containing an absorber. Two side edges of the outer member in the front body and two side edges of the outer member in the back body are bonded together at side seal portions to define a waist opening, a left leg opening, and a right leg opening.

In such an underpants-type disposable diaper, the outer member has a layered structure including several sheet layers and various elongated elastic members stretched and fixed between the sheet layers to provide a stretchable structure to enhance the fit to the body. Some underpants-type disposable diapers having elongated elastic members fixed in the width direction at predetermined intervals in the front-back direction in front and back lower torso regions each defined by a corresponding region in the front-back direction to the side seal portions and an intermediate region disposed between the front and back lower torso regions have a relatively tight fit to the body (for example refer to Patent Document 1).

The lower torso regions and the intermediate region overlap with a range in the front-back direction containing the absorber and also contain stationary portions at which the inner member is fixed to the outer member in the range. Thus, the stretch and contraction of the elastic members extending across the range in the front-back direction containing the absorber are limited by the stiffness of the absorber. The absorber may contract in the width direction causing unsatisfactory fitting and appearance of the diaper; or the absorber may wrinkle or crack causing reduction in the absorption ability.

Thus, typically, the elastic members are fixed continuously in the width direction and those disposed over the absorber are substantially entirely snicked, or unfixed to the outer member in an area over the absorber and cut at one intermediate position in the width direction, to define a non-stretchable region in which the contracting force is not applied to the absorber in the width direction. The elastic members are cut by a technique that does not form holes in the inner sheet layer and the outer sheet layer covering the inner and outer faces of the elastic members. An example technique for cutting is to apply pressure and heat at cutting positions on inner and outer faces of the elastic members disposed between the inner sheet layer and the outer sheet layer.

The contracting force of the elastic members in the non-stretchable region on the outer member is substantially ineffective and thus substantially no contraction wrinkles are formed. Thus, the non-stretchable region has high transmittance of light compared to other regions having contraction wrinkles. Thus, a graphic sheet having illustrations is disposed between sheet layers of the outer member in this region (refer to Patent Document 1 and 2).

Since the graphic sheet is viewed through the material of the outer member, it is preferred that the graphic sheet and the elastic members be disposed between the sheet layers of the outer member in consideration of visibility of the graphical illustration. In such a case, the graphic sheet is adjacent to the elastic members; hence, it is preferred that the elastic members not be fixed to the graphic sheet or be weakly fixed to be readily unfixed, to completely remove the influence of the contracting force of the elastic members.

In such a case, the elastic members should be cut while the elastic members and the graphic sheet are disposed between the outer sheet layer and the inner sheet layer. However, cutting the elastic members over the graphic sheet by pressure and heat, as described in PTL 1 and 2, is problematic in the following aspects.

In the case that all elastic members to be cut extend over the graphic sheet, no problem arises. However, in the case that some of the elastic members to be cut extend over a region not overlapping with the graphic sheet, the thickness of the layers to receive the pressure is smaller by the thickness of the graphic sheet, thereby slightly reducing the pressure applied to the elastic members. As a result, these elastic members are not cut. In other words, some of the elastic members remain uncut in the region not overlapping with the graphic sheet.

All elastic members can be cut by increasing the pressure to be applied during the cutting step. However, an increase in cutting pressure is not preferred because the sheet layers will be partially cut and/or apparent cut marks will form.

If the bonding of the inner sheet layer and the outer sheet layer and/or the fixing of the elastic members to the inner sheet layer and the outer sheet layer are omitted or weakened so as to increase flexibility in an outer member having a structure separated in the front-back direction into a front outer member of the front body and a back outer member of the back body, the gap between the inner sheet layer and the outer sheet layer opens to the crotch side and causes not only unattractive appearance but also protrusion or fall out of idle elastic members from the opening.

CITATION LIST—PATENT DOCUMENT

Patent Document 1: Japanese Patent Application Laid-open Publication No. 2004-298362

Patent Document 2: Japanese Patent Application Laid-open Publication No. 2004-254861

Patent Document 3: Japanese Patent Application Laid-open Publication No. 2010-158590

SUMMARY OF INVENTION

Technical Problem

An object of the present invention is to prevent incomplete cutting of elastic members in an outer member including a graphic sheet in a non-stretchable region.

Solution to Problem

The present invention, which provides solutions to the issues described above, is described below.

<The Invention of Claim 1>

An underpants-type disposable diaper comprising:

a front outer member disposed in a front body and a back outer member disposed in a back body, the front outer member and the back outer member comprising a single segment or two discrete segments; and an inner member disposed from the front outer member to the back outer member, the inner member containing an absorber, wherein, two side edges of the front outer member and two side edges of the back outer member are bonded together so as to define a waist opening, a left leg opening, and a right leg opening, at least one of the front outer member and the back outer member has, in a range in the front-back direction containing the absorber, a non-stretchable region at an intermediate position in the width direction and two stretchable regions disposed on two sides of the non-stretchable region in the width direction, the stretchable region is defined by an inner sheet layer, an outer sheet layer, and elongated elastic members fixed in a stretched state in the width direction at intervals in the front-back direction between the inner sheet layer and the outer sheet layer, the non-stretchable region is defined by the inner sheet layer and the outer sheet layer continuing from the stretchable region, a graphic sheet disposed between the inner sheet layer and the outer sheet layer and visible through the outer face, and idle elastic members having at least one of each residual portion continuing from the corresponding elastic member in the stretchable region and each cut fragment separated from the corresponding elastic member in the two stretchable regions, the stretchable regions and the non-stretchable region extend over a corresponding range in the front-back direction to the graphic sheet and at least one of the front side and the back side thereof;

wherein at least one no-extra-sheet region is defined by a side portion of the non-stretchable region extending outward from one side of the graphic sheet in the width direction, and the no-extra-sheet region contains no other sheet between the inner sheet layer and the outer sheet layer, and wherein a region overlapping with the graphic sheet has no cut mark of the elastic members and the no-extra-sheet region has cut marks of the elastic members.

Advantageous Effects

In the present invention, the cutting positions of the elastic members in the non-stretchable region are disposed in the no-extra-sheet regions in which the graphic sheet and other sheets are absent; thus, the thickness of the target to receive pressure, i.e., the pressure applied to the cutting target is uniform in the front-back direction even if the elastic members, which are the cutting targets, are disposed over the corresponding range in the front-back direction to the graphic sheet and at least one of the front side and the back side thereof. Thus, incomplete cutting of the elastic members will barely occur even if the graphic sheet is disposed between the inner sheet layer and the outer sheet layer in the non-stretchable region of each outer member. The absence of cut marks of the elastic members over the graphic sheet achieved a satisfactory appearance of the graphic sheet.

<The Invention of Claim 2>

The underpants-type disposable diaper according to claim 1, wherein the cut marks of the elastic members continue in the front-back direction at least from a cutting position of the elastic member closest to the waist opening to a cutting position of the elastic member closest to a crotch.

Advantageous Effects

In this case, the elastic members are cut in a continuous pressurizing pattern. Thus, the elastic members can be prevented from shifting away from the pressurizing positions and remaining uncut.

<The Invention of Claim 3>

The underpants-type disposable diaper according to claim 1 or 2, wherein, the front outer member is separate from the back outer member in the front-back direction, the at least one no-extra-sheet region comprises two no-extra-sheet regions disposed on two sides of the graphic sheet in the width direction, and the cut marks are disposed in the no-extra-sheet regions on the two sides of the graphic sheet, and a welded portion of the inner sheet layer and the outer sheet layer is disposed at an area on the crotch side of the idle elastic members.

Advantageous Effects

In particular, cutting of the elastic members at the two sides of the graphic sheet in the width direction causes the idle elastic members to consist of only cut fragments not continuous from the elastic members in the stretchable regions on the two sides. This emphasizes the boundaries of the stretchable regions and the non-stretchable region and achieves a satisfactory appearance. In the case where the front outer member and the back outer member are separately provided in the front-back direction, the gap between the inner sheet layer and the outer sheet layer opens at the edge adjacent to the crotch if the bonding of the inner sheet layer and the outer sheet layer and/or the fixing of the elastic members to the inner sheet layer and the outer sheet layer are omitted or weakened to enhance flexibility. This causes an unattractive appearance and also the idle elastic members to protrude from or fall out of the opening. In contrast, a welded portion disposed between the idle elastic members and the crotch edge and welding the inner sheet layer and the outer sheet layer, as described above, completely or partially close the crotch-side opening of the gap between the inner sheet layer and the outer sheet layer. This is preferred because it prevents unattractive appearance and uncomfortable fitting and protrusion or fall out of the idle elastic members.

<The Invention of Claim 4>

The underpants-type disposable diaper according to claim 3, wherein the inner sheet layer and the outer sheet layer are continuously welded from one of the cut marks to the other cut mark through the welded portion into a U-shape.

Advantageous Effects

Welding in such a U-shaped pattern not only cuts the elastic members and welds the area on the crotch side of the idle elastic members at the same time but also a welded portion surrounding the idle elastic members is formed to effectively prevent protrusion and/or fall out the idle elastic members. This also prevents incomplete cutting of the elastic members.

<The Invention of Claim 5>

A method of producing the underpants-type disposable diaper according to claim 1, the method comprising
forming an outer member, by:
disposing the graphic sheet between the inner sheet layer and the outer sheet layer in a portion to be the non-stretchable region;
disposing the elongated elastic members between the inner sheet layer and the outer sheet layer continuously over a portion to be the stretchable region, the portion to be the non-stretchable region, a portion overlapping with the graphic sheet, and a portion to be the at least one no-extra-sheet region;
fixing the elastic members with a hot-melt adhesive agent to the inner sheet layer and the outer sheet layer in at least two edge portions of the portions to be the stretchable regions without fixing the elastic members to the inner sheet layer nor the outer sheet layer in the portion to be the non-stretchable region;
subsequently, cutting the elastic members extending over the portion to be the no-extra-sheet region by clamping the inner face of the inner sheet layer and the outer face of the outer sheet layer in the portion to be the no-extra-sheet region and applying pressure and heat; and
leaving the elastic members in the region overlapping with the graphic sheet uncut without application of pressure or heat.

Advantageous Effects

In the present invention, the cutting positions of the elastic members in the non-stretchable region are disposed in the no-extra-sheet regions in which the graphic sheet and other sheets are absent; thus, the thickness of the target to receive pressure, i.e., the pressure applied to the cutting target is uniform in the front-back direction even if the elastic members, which are the cutting targets, are disposed over the corresponding range in the front-back direction to the graphic sheet and at least one of the front side and the back side thereof. Thus, incomplete cutting of the elastic members will barely occur even if the graphic sheet is disposed between the inner sheet layer and the outer sheet layer in the non-stretchable region of each outer member. Since the cut marks of the elastic members do not remain over the graphic sheet, the graphic sheet has a satisfactory appearance. The term "not fixed" referring to the elastic members will be defined below.

<The Invention of Claim 6>

The method according to claim 5, further comprising:
prior to cutting the elastic members, preventing shift of the elastic members by fixing the elastic members to the inner sheet layer and the outer sheet layer in a region containing a portion to be the cutting positions with a shift-preventing hot-melt adhesive agent; and
subsequently, cutting the elastic members in an intermediate region of the shift-preventing hot-melt adhesive agent in the width direction and causing the elastic members to contract against the adhesive force of the shift-preventing hot-melt adhesive agent due to the contracting force of the elastic members.

Advantageous Effects

Preventing shift of the elastic members with the shift-preventing hot-melt adhesive agent in the no-extra-sheet region containing the portions to be the cutting positions prevents displacement of the elastic members during cutting, and thus more precise cutting is achieved. The cut ends adjacent to the stretchable regions contract toward the stretchable regions after cutting of the elastic members. The pulling force of the elastic members weakens as the cut ends are pulled in, and thus, the ends of the elastic members in the stretchable regions are not readily unfixed.

<The Invention of Claim 7>

The method according to claim 5 or 6, wherein the pressure and heat are applied in a linear pattern continuous in the front-back direction at least from the cutting position of the elastic member closest to the waist opening to the cutting position of the elastic member closest to the crotch.

Advantageous Effects

In this case, the elastic members are cut in a continuous pressurizing pattern. Thus, the elastic members can be prevented from shifting away from the pressurizing positions and remaining uncut.

<The Invention of Claim 8>

The method according to one of claims 5 to 7, wherein the underpants-type disposable diaper is set forth in claim 3, comprising:
cutting the elastic members by clamping the inner face of the inner sheet layer and the outer face of the outer sheet layer and applying pressure and heat to the corresponding range in the front-back direction to the graphic sheet and at least one of the front side and the back side thereof in portions at the both sides in the width direction to be the two no-extra-sheet regions; and
clamping the inner face of the inner sheet layer and the outer face of the outer sheet layer and applying pressure and heat to the inner and outer sheet layers to weld the inner sheet layer and the outer sheet layer at a crotch-side edge portion of the portion to be the non-stretchable region.

Advantageous Effects

In particular, cutting of the elastic members at the sides of the graphic sheet in the width direction causes the idle elastic members to consist of only cut fragments of the elastic members not continuous from the elastic members in the stretchable regions on the two sides. This emphasizes the boundaries of the stretchable regions and the non-stretchable region and achieves a satisfactory appearance. In the case where the front outer member and the back outer member are separately provided in the front-back direction, the gap between the inner sheet layer and the outer sheet layer opens at the edge adjacent to the crotch if the bonding of the inner sheet layer and the outer sheet layer and/or the fixing of the elastic members to the inner sheet layer and the outer sheet layer are omitted or weakened to enhance flexibility. This causes an unattractive appearance and also the idle elastic members to protrude from or fall out of the opening. In contrast, a welded portion disposed between the idle elastic members and the crotch edge and welding the inner sheet layer and the outer sheet layer, as described above, completely or partially close the crotch-side opening of the gap between the inner sheet layer and the outer sheet layer. This is preferred because it prevents unattractive appearance and uncomfortable fitting and protrusion or fall out of the idle elastic members.

<The Invention of Claim 9>

The method according to claim 8, further comprising:

clamping the inner face of the inner sheet layer and the outer face of the outer sheet layer and applying pressure and heat to a continuous U-shape from one of portions to be the no-extra-sheet regions to the other portion to be the no-extra-sheet region through a crotch-side portion of the portion to be the non-stretchable region to cut the elastic members and weld the inner sheet layer and the outer sheet layer.

Advantageous Effects

Welding in such a U-shaped pattern not only cuts the elastic members and welds the area on the crotch side of the idle elastic members at the same time but also a bonded portion section surrounding the idle elastic members is formed to effectively prevent protrusion and/or fall out the idle elastic members. This also prevents incomplete cutting of the elastic members.

Advantageous Effects of Invention

As described above, the present invention is advantageous in that incomplete cutting of elastic members in the outer body including a graphic sheet in a non-stretchable can be prevented and so on.

BRIEF DESCRIPTION OF DRAWINGS

FIG. 5(*b*) is a cross-sectional view taken along line 6-6 in FIG. 1.

FIG. 9(*a*) is a plan view of elastic members after cutting; FIG. 9(*b*) is a cross-sectional view of the elastic members after cutting; and FIG. 9(*c*) is a cross-sectional view of the elastic members before cutting.

FIG. 10(*a*) is a plan view of the elastic members after cutting; FIG. 10(*b*) is a cross-sectional view of the elastic members after cutting; and FIG. 10(*c*) is a cross-sectional view of the elastic members before cutting.

FIG. 11(*a*) is a plan view of the elastic members after cutting; FIG. 11(*b*) is a cross-sectional view of the elastic members after cutting; and FIG. 11(*c*) is a cross-sectional view of the elastic members before cutting.

FIG. 12(*a*) is a plan view of the elastic members after cutting; FIG. 12(*b*) is a cross-sectional view of the elastic members after cutting; and FIG. 12(*c*) is a cross-sectional view of the elastic members before cutting.

FIG. 13(*a*) is a plan view of the elastic members after cutting; FIG. 13(*b*) is a cross-sectional view of the elastic members after cutting; and FIG. 13(*c*) is a cross-sectional view of the elastic members before cutting.

DESCRIPTION OF EMBODIMENTS

Figure 1:
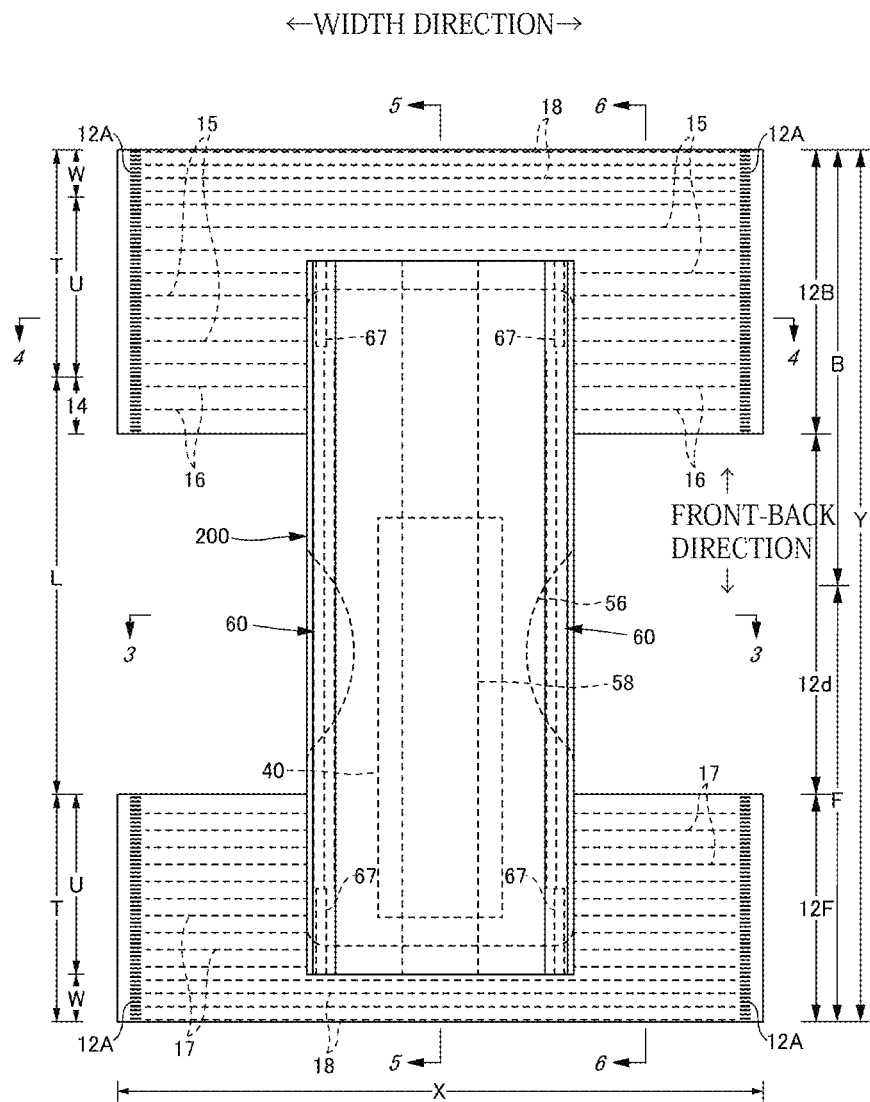
FIG. 1 is a plan view of the inner face of an underpants-type disposable diaper in a spread state.

Embodiments of the present invention will now be described in detail with reference to the accompanying drawings.

FIGS. 1 to 6 illustrate an example underpants-type disposable diaper 100. The dot patterns in the cross-sectional views indicate adhesive patterns serving as bonding means of components on the front and back faces. The adhesive patterns are formed through solid, bead, curtain, summit, or spiral application of a hot-melt adhesive agent, or pattern application (transfer of the hot-melt adhesive agent by relief printing), and the elastic members are fixed at fixed portions through such application of the adhesive agent and/or application of the adhesive agent with a comb gun or a Surewrap nozzle to the circumferential face of the elastic members. Any hot-melt adhesive agent may be used. Examples of such a hot-melt adhesive agent include various types of adhesives based on, for example, EVA, adhesive rubber (elastomers), olefins, polyesters, and polyamides. The bonding means for bonding the components may be any means for welding materials, such as heat sealing or ultrasonic sealing.

The underpants-type disposable diaper 100 according to this embodiment includes a front outer member 12F disposed in a front body F, a back outer member 12B disposed in a back body B, and an inner member 200 extending from the front outer member 12F to the back outer member 12B through the crotch portion and having a front edge fixed to the front outer member 12F and a back edge fixed to the back outer member 12B. The two side edges of the front outer member 12F are bonded to the respective side edges of the back outer member 12B to form side seal portions 12A. The opening defined by the front and back edges of the outer members 12F and 12B serves as a waist opening WO through which the torso of the wearer passes, and the openings defined by the lower edges of the outer members 12F and 12B and the side edges of the inner member 200 at the two side edges of the inner member 200 in the width direction serve as leg openings LO through which the legs of the wearer pass. The inner member 200 absorbs and retains excretion, such as urine, and the outer member 12 supports the inner member 200 on the body of the wearer. The reference sign Y indicates the entire length of the diaper in a spread state (the front-back length from the edge of the waist opening WO of the front body F to the edge of the waist opening WO of the back body B), and the reference sign X indicates the overall width of the diaper in a spread state.

The underpants-type disposable diaper 100 according to this embodiment includes a lower torso region T defined as a range in the front-back direction including the side seal portions 12A (a range in the front-back direction from the waist opening WO to the upper edges of the leg openings LO) and an intermediate region L defined as a range in the front-back direction forming the leg openings LO (the region between the region in the front-back direction including the side seal portions 12A of the front body F and the region in the front-back direction including the side seal portions 12A of the back body B). The lower torso region T can be conceptually separated into a "waist portion" W forming the edge of the waist opening and an "under-waist portion" U disposed below the waist portion W. Usually, in the case where the lower torso region T includes boundaries undergoing variations in expansion and contraction stress along the width direction (for example, variations in the fineness or the stretch rate of the elastic members), the area between the boundary closest to the waist opening WO and the waist opening WO is defined as the waist portion W. In the case where such boundaries are absent, the area between an absorber 56 or the inner member 200 and the waist opening WO is defined as the waist portion W. The front-back lengths of such portions depend on the dimensions of the product and can be appropriately determined. For example, the front-back length may be within the range of 15 to 40 mm for the waist portion W and 65 to 120 mm for the under-waist portion U. The two side edges of the intermediate region L are formed to be generally square channel-shaped or narrowed to fit around the legs of the wearer and define openings through which the legs of the wearer pass. As a result, the underpants-type disposable diaper in a spread state has an overall shape similar to the outline of an hourglass.

(Inner Member)

Figure 3:
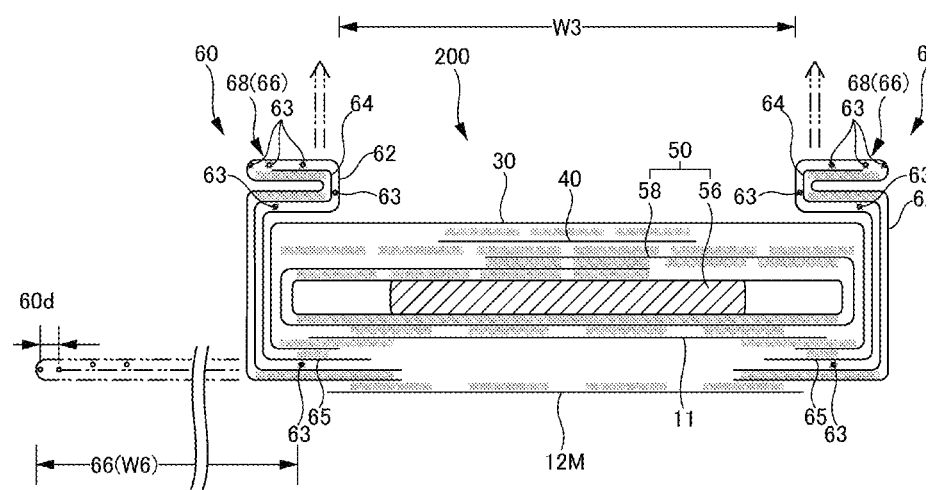
FIG. 3 is a cross-sectional view taken along line 3-3 in FIG. 1.
Figure 4:
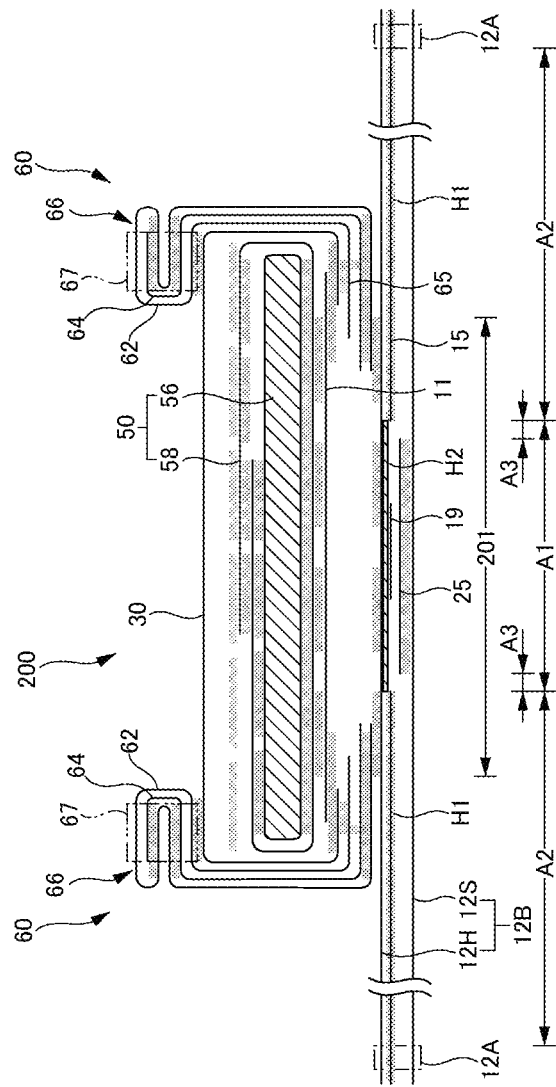
FIG. 4 is a cross-sectional view take along line 4-4 in FIG. 1.
Figure 5:
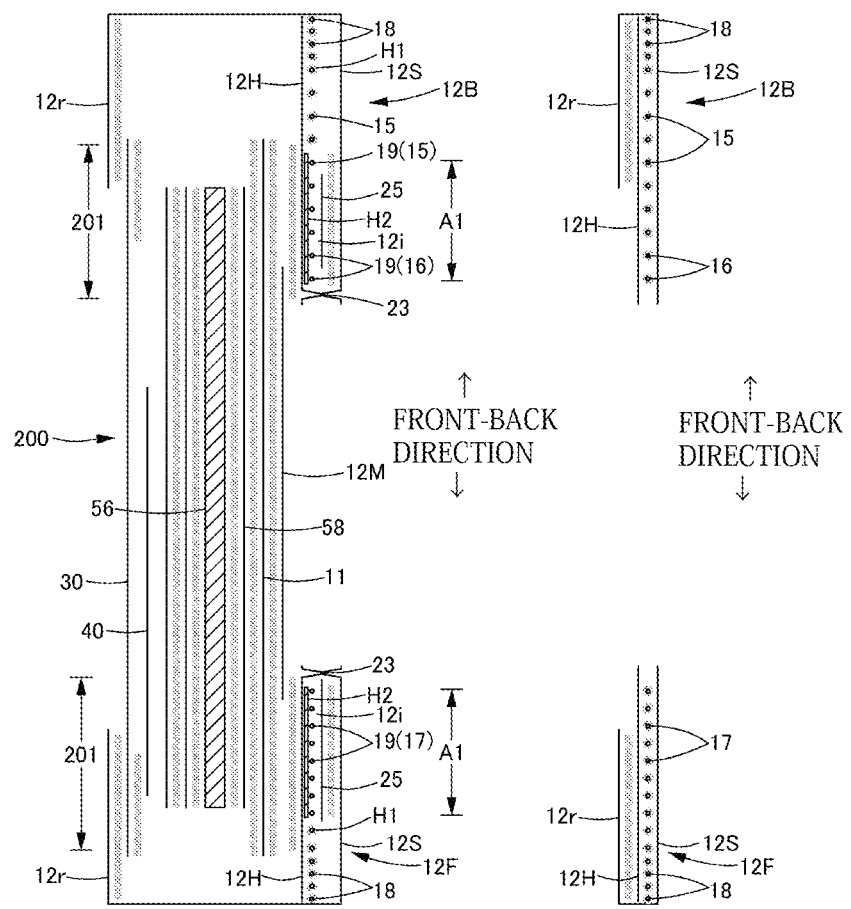
FIG. 5(*a*) is a cross-sectional view taken along line 5-5 in FIG. 1.
Figure 6:
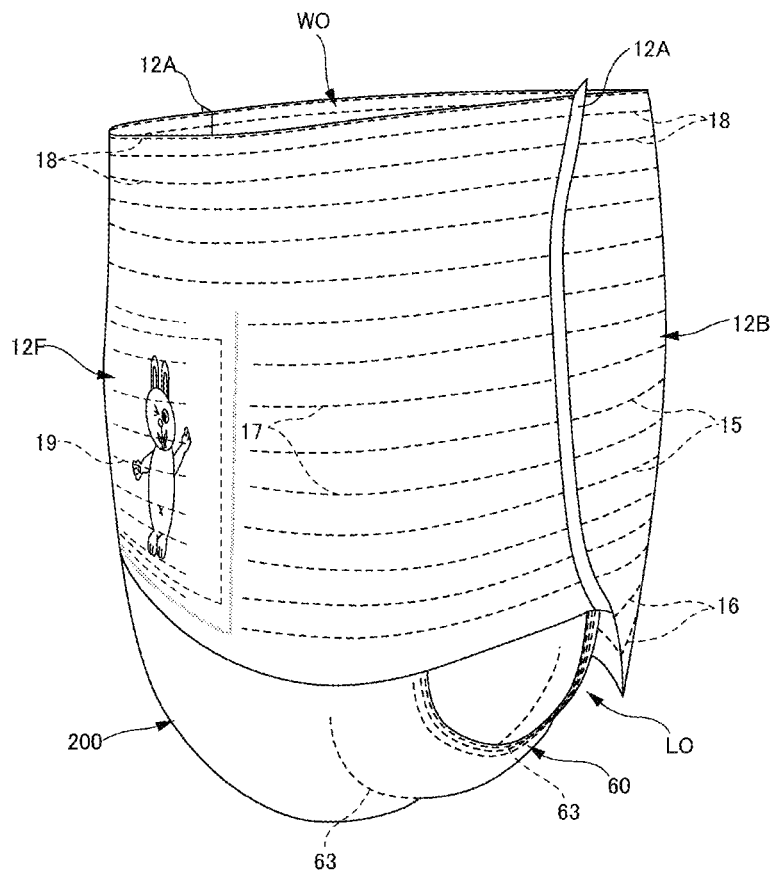
FIG. 6 is a perspective view of the underpants-type disposable diaper.

The inner member 200 may have any shape. In this embodiment, the inner member 200 has a rectangular shape. The inner member 200 includes a liquid pervious top sheet 30 adjacent to the body of the wearer, a liquid impervious sheet 11, and an absorber element 50 disposed therebetween, as illustrated in FIGS. 3 to 5. The inner member 200 is the main section that provides an absorbing function. Reference sign 40 represents an intermediate sheet (second sheet) disposed between the top sheet 30 and the absorber element 50 for prompted migration of the liquid passing through the top sheet 30 into the absorber element 50, and reference sign 60 represents three-dimensional gathers 60 that extend along the two edges of the inner member 200 and erect around the body of the wearer, to prevent leakage of excretion from the two edges of the inner member 200.

To the outer members 12F and 12B, the inner member 200 can be fixed by a bonding means for welding materials, such as heat sealing or ultrasonic sealing, or with a hot-melt adhesive agent. In the illustrated embodiments, the inner member 200 is fixed to the inner face of the outer member 12 with a hot-melt adhesive agent applied to the back face of the inner member 200, which is the back face of the liquid impervious sheet 11 and attachments 65 of the three-dimensional gathers 60 in this case. Stationary portions 201 that fix the inner member 200 to the outer members 12F and 12B can be provided in substantially the entire overlapping area of the members. It is usually preferred to provide the stationary portions 201 in regions other than the two side portions of the inner member in the width direction.

(Top Sheet)

The top sheet 30 may be composed of any liquid pervious materials, such as porous or non-porous non-woven fabric and a porous plastic sheet. The nonwoven fabric may be composed of any raw fiber. Examples of such raw fiber include synthetic fibers based on olefins, such as polyethylene and polypropylene, polyesters, and polyamides; recycled fibers, such as rayon and cupra; natural fibers, such as cotton; and mixed fibers and composite fibers composed of two or more of these fibers. The non-woven fabric may be produced through any process. Examples of known processes include spunlacing, spunbonding, thermal bonding, melt blowing, needle punching, air through bonding, and point bonding. For example, spunbonding and spunlacing are suitable for achieving flexibility and draping, whereas air through bonding, point bonding, and thermal bonding are suitable for bulkiness and softness.

The top sheet 30 may be composed of a single-layer sheet or a layered sheet formed by laminating two or more sheets to each other. Similarly, the top sheet 30 may be composed of a single sheet or two or more sheets in a planar direction.

In the case where the three-dimensional gathers 60 are provided, it is preferred that the two side edges of the top sheet 30 extend between the liquid impervious sheet 11 and the three-dimensional gathers 60 and to the back face of the absorber element 50 and be bonded to the liquid impervious sheet 11 and the three-dimensional gathers 60, to prevent permeation of liquid.

It is preferred that the top sheet 30 be fixed to a component adjacent to the back face of the top sheet 30 by a bonding means for welding materials, such as heat sealing or ultrasonic sealing, or with a hot-melt adhesive agent, to prevent shift relative to the back-face component. In the illustrated embodiments, the top sheet 30 is fixed to the front face of an intermediate sheet 40 and an area on the front face of a wrapping sheet 58 extending over the absorber 56 with a hot-melt adhesive agent applied to the back face of the top sheet 30.

(Intermediate Sheet)

An intermediate sheet (also referred to as "second sheet") 40 having a liquid permeation rate higher than that of the top sheet 30 may be provided for prompted migration of liquid from the top sheet 30 to the absorber. The intermediate sheet 40 not only increases the absorption ability by prompted migration of liquid to the absorber but also prevents returning of liquid from the absorber and maintains the top sheet 30 in a constantly dry state. The intermediate sheet 40 may be omitted.

Examples of materials for the intermediate sheet 40 include the same materials for the top sheet 30, spunlace fabric, spunbond fabric, SMS, pulp non-woven fabric, a sheet composed of a mixture of pulp and rayon, pointbond fabric, and crepe paper. Air-through non-woven fabric is particularly preferred for its bulkiness. Air-through non-woven fabric is preferably composed of composite fibers having a core-in-sheath structure. In such a case, the core is composed of a resin, such as polypropylene (PP), preferably polyester (PET) having high stiffness. The basis weight is preferably within the range of 20 to 80 $g/m^2$, more preferably 25 to 60 $g/m^2$. The fineness of the raw fibers of the non-woven fabric is preferably within the range of 2.0 to 10 dtex. For the bulkiness of the non-woven fabric, it is preferred that all or some of the raw fibers be mixed fibers, such as offset-core fibers having an eccentric core, hollow fibers, or hollow off-set core fibers.

The intermediate sheet 40 according to the illustrated embodiments has a width smaller than that of the absorber 56 and is disposed in the central area. Alternatively, the intermediate sheet 40 may be disposed over the maximum width. The intermediate sheet 40 may have a longitudinal length the same as that of the absorber 56 or may have a small length centered on the section receiving liquid.

It is preferred that the intermediate sheet 40 be fixed to a component adjacent to the back face by a bonding means for welding materials, such as heat sealing or ultrasonic sealing, or with a hot-melt adhesive agent, to prevent shift relative to the back face component. In the illustrated embodiments, the intermediate sheet 40 is fixed to an area on the front face of the wrapping sheet 58 extending over the absorber 56 with a hot-melt adhesive agent applied to the back face of the intermediate sheet 40.

(Liquid Impervious Sheet)

The liquid impervious sheet 11 may be composed of any material. Examples of such a material include a plastic film composed of an olefin resin, such as a polyethylene resin or a polypropylene resin, laminated non-woven fabric composed of non-woven fabric applied with a plastic film, and a laminated sheet composed of a plastic film and non-woven fabric. It is preferred that the liquid impervious sheet 11 be composed of a material having liquid imperviousness and moisture permeability, which is preferred in view of prevention of stuffiness. An example of a common plastic film having moisture permeability is a microporous plastic film produced by kneading an olefin resin, such as a polyethylene resin or a polypropylene resin, and an inorganic filler, forming a sheet with the kneaded materials, and monoaxially or biaxially stretching the sheet. Other examples of the material of the liquid impervious sheet 11 include non-woven fabric of microdenier fiber and a liquid impervious sheet without a plastic film having reinforced antileakage properties achieved by applying heat and/or pressure to reduce the gaps between the fibers or by application with super absorbent resin, hydrophobic resin, or a water repellent.

The liquid impervious sheet 11 may have a width smaller than the width of the back face of the absorber element 50, as illustrated in the drawings. Alternatively, the liquid impervious sheet 11 may be turned up at the two side faces of the absorber element 50 to extend to side portions of the top sheet 30 to enhance antileakage properties. The proper width of the extending portions on the left and the right may be within the range of approximately 5 to 20 mm.

The inner face of the liquid impervious sheet 11, in particular the face adjacent to the absorber 56 may be provided with an excretion indicator that changes color in response to absorption of liquid.

(Three-Dimensional Gathers)

The three-dimensional gathers 60 are strips extending along the two side edges of the inner member 200 along the entire length in the front-back direction. The three-dimensional gathers 60 prevent side leakage of excretion due to lateral migration of the excretion along the top sheet 30. The three-dimensional gathers 60 according to this embodiment are erectly disposed on the side portions of the inner member 200. The proximal portions of the three-dimensional gathers 60 obliquely extend inward toward the center in the width direction and the distal halves of the three-dimensional gathers 60 obliquely extend outward in the width direction.

In detail, each of the three-dimensional gathers 60 includes a strip gather sheet 62 having a length equal to the front-back length of the inner member 200 and folded back once in the width direction; and multiple elongated gather elastic members 63 fixed in a stretched state in the longitudinal direction between sheets in the folded portion and the neighboring region in the longitudinal direction at predetermined intervals in the width direction. The base portion of the three-dimensional gather 60 opposite to the tip portion (the second edge opposite to the first edge in the folded portion in the width direction) serves as an attachment 65 fixed to the back face of each side edge portion of the inner member 200. The portion of the three-dimensional gather 60 other than the attachment 65 is defined as a protruding portion 66 (folded portion) protruding from the attachment 65. The protruding portion 66 includes the proximal portion extending toward the center in the width direction and a distal portion folded back at the distal edge of the proximal portion outward in the width direction. The three-dimensional gathers according to this embodiment are of an areal contact type. Alternatively, the three-dimensional gathers may be of a line contact type (not shown) in which the three-dimensional gathers are not folded outward in the width direction. The end portions of the protruding portions 66 in the front-back direction define front-back fixed portions 67 folded and fixed to the face of the edge portions of the top sheet 30. The intermediate portion in the front-back direction between the two front-back fixed portions 67 of each protruding portion 66 defines an unfixed free portion 68. The gather elastic members 63 are fixed in a stretched state to the free portion 68 in the front-back direction.

In the free portion 68 of the three-dimensional gather 60, the bonding of the inner layer and the outer layer of the gather sheets 62 and the fixing of the gather elastic members 63 between the inner layer and the outer layer can be achieved with at least one of a hot-melt adhesive agent applied through any means and by a fixing means for welding materials, such as heat sealing and ultrasonic sealing. Bonding of the entire faces of the inner layer and the outer layer of the gather sheet 62 reduces flexibility. Thus, it is preferred that the areas other than the bonding areas of the gather elastic members 63 be weakly bonded or not bonded at all. In the illustrated embodiments, a hot-melt adhesive agent is applied to only to the circumferential faces of the gather elastic members 63 with an application tool, such as a comb gun or a Surewrap nozzle, and then the gather elastic members 63 are disposed between the inner layer and the outer layer of the gather sheets 62. In this way, the elongated elastic members are fixed to the inner layer and the outer layer of the gather sheet 62 and the inner layer is fixed to the outer layer by merely applying a hot-melt adhesive agent to the circumferential faces of the gather elastic members 63.

A waterproof film 64 can be fixed to the gather sheet 62 of the three-dimensional gathers 60 and the front-back fixed portion 67 can be fixed to the front face of edge portions of the inner member 200 with at least one of a hot-melt adhesive agent applied by any means and by a fixing means for welding materials, such as heat sealing and ultrasonic sealing. In the illustrated embodiments, the waterproof film 64 is fixed through slot application of the hot-melt adhesive agent. The front-back fixed portion 67 in the illustrated embodiments is fixed through a combination of the hot-melt adhesive agent and a means for welding materials. Alternatively, the fixing may be achieved through either application of the hot-melt adhesive agent or the means for welding materials.

The gather sheets 62 may be composed of flexible, uniform non-woven fabric having satisfactory sealing properties, such as spunbond non-woven fabrics (SS, SSS and the like), SMS non-woven fabrics (SMS, SSMMS and the like), and meltblown non-woven fabrics, provided with a water repellent finish using silicone, for example, as required. The fiber basis weight is preferably within the range of approximately 10 to 30 g/m². The elongated elastic members 63 may be composed of rubber threads. In a case where spandex rubber threads are used, the fineness is preferably within the range of 470 to 1240 dtex, more preferably 620 to 940 dtex. The stretch rate in a fixed state is preferably within the range of 150% to 350%, more preferably 200% to 300%. The term "stretch rate" refers to a relative value when a natural length is set to 100%. The waterproof films 64 may be disposed between the folded portions of the gather sheet, as illustrated in the drawings.

The number of the elongated elastic members 63 to be disposed in the free portion of each three-dimensional gather 60 is preferably 2 to 6, more preferably 3 to 5. The intervals 60d thereof are preferably within the range of 3 to 10 mm. Such a configuration causes the area containing the elongated elastic members 63 to readily come into areal contact with the skin of the wearer. The elongated elastic members 63 may be disposed not only in the distal portion but also in the proximal portion.

The attachment 65 of the three-dimensional gather 60 may be fixed to any appropriate component of the inner member 200, such as the top sheet 30, the liquid impervious sheet 11, or the absorber element 50.

In the three-dimensional gather 60 having such a configuration, the contracting force of the elongated elastic members 63 moves the two end portions close to each other in the front-back direction. The end portions of the protruding portion 66 are fixed and prevented from being erected. The free portion between the end portions are not fixed. Thus, only the free portion erects so as to come into contact with the body of the wearer, as illustrated in FIG. 3. In specific, the attachment 65, which is disposed on the back face of the inner member 200, causes the three-dimensional gather 60 to erect outward in the width direction along and near the crotch. This causes the three-dimensional gather 60 to come into areal contact with the circumference of the corresponding leg of the wearer, thereby enhancing the fit of the diaper.

The dimensions of the three-dimensional gathers 60 can be appropriately selected. For disposable baby diapers, the vertical length W6 of each three-dimensional gather 60 (the width of the corresponding protruding portion 66 in a spread state) is in the range of 15 to 60 mm, preferably 20 to 40 mm. The distance W3 between the innermost crease of the three-dimensional gather 60 folded into a flat state such that the three-dimensional gather 60 is parallel to the front face of the top sheet 30 is preferably within the range of the 60 to 190 mm, more preferably 70 to 140 mm.

Alternative to the illustrated embodiments, two layers (two rows) of the three-dimensional gathers may be provided on each of the right and left sides of the inner member 200.

(Absorber Element)

The absorber element 50 includes an absorber 56 and a wrapping sheet 58 covering the entire absorber 56. The wrapping sheet 58 may be omitted.

(Absorber)

The absorber 56 may be composed of a fiber assembly. Examples of the fiber assembly include an assembly of fluff pulp, short fibers, such as synthetic fibers, assembled through fiber accumulating, and an assembly of filaments acquired through opening tows (fiber bundles) of synthetic fibers, such as cellulose acetate, as required. The fiber basis weight of accumulated fluff pulp or short fibers may be within the range of approximately 100 to 300 g/m$^2$, and the fiber basis weight of a filament assembly may be within the range of approximately 30 to 120 g/m$^2$, for example. The fineness of synthetic fiber is, for example, within the range of 1 to 16 dtex, preferably 1 to 10 dtex, more preferably 1 to 5 dtex. Although the filaments in a filament assembly may be composed of non-crimped fiber, it should preferably be crimped fiber. The degree of crimp of the crimped fiber is, for example, within the range of 5 to 75 per inch, preferably 10 to 50 per inch, more preferably 15 to 50 per inch. Uniformly crimped fiber is often used. It is preferred that super absorbent polymer particles be dispersed in the absorber 56.

Figure 2:
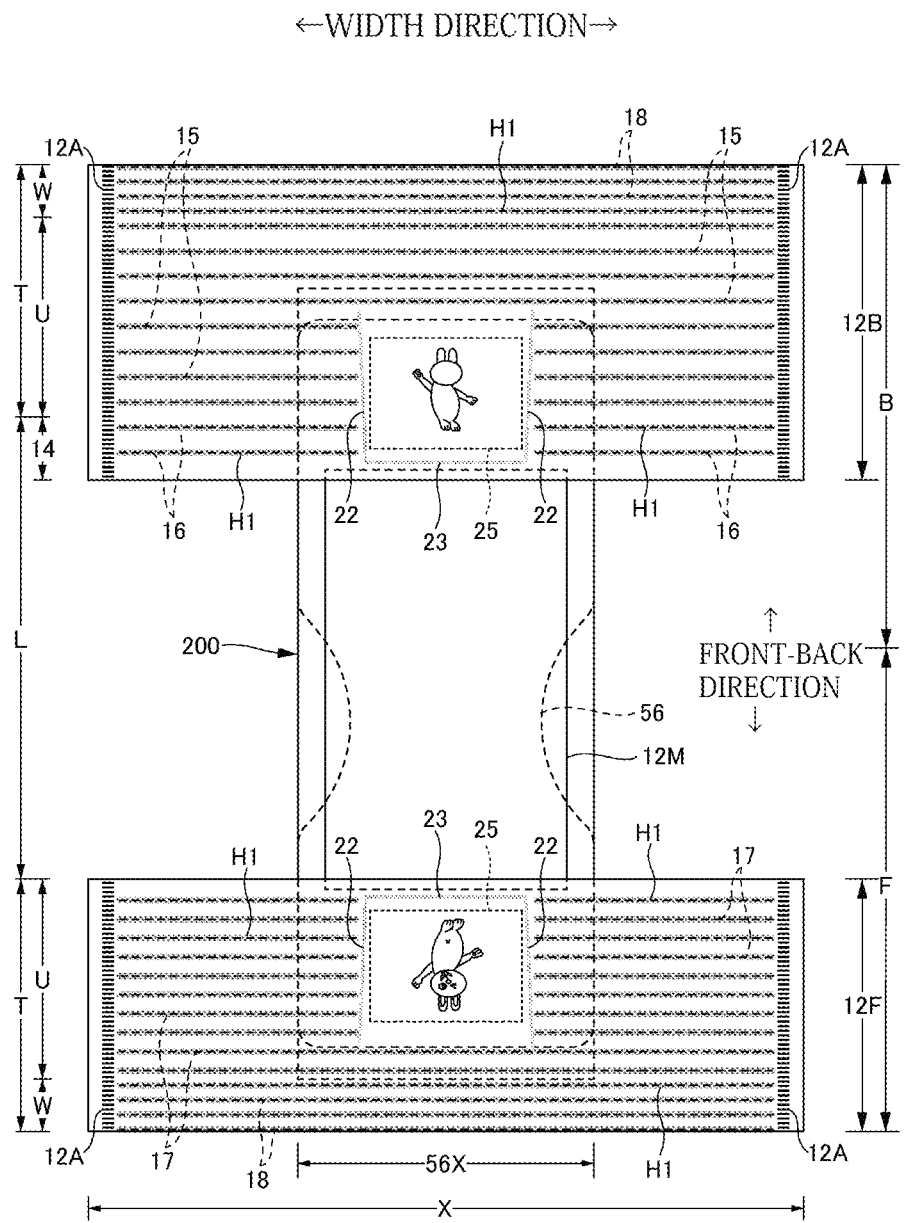
FIG. 2 is a plan view of the outer face of the underpants-type disposable diaper in a spread state.

The absorber 56 may have a rectangular shape. It is preferred that the absorber 56 be disposed on and between the front end portion and the back end portion and have a shape similar to the outline of an hourglass in which a narrowing portion has a width smaller than that of the front end portion and the back end portion, as illustrated in FIGS. 1 and 2, because the fit of the absorber 56 and the three-dimensional gathers 60 to the legs is enhanced.

The absorber 56 may have any appropriate dimensions extending over the position of the urethral orifice of the wearer. It is preferred that the absorber 56 extends in the front-back and width directions to the peripheral edges of the inner member or the neighboring region thereof. Reference sign 56X represents the width of the absorber 56.

(Super Absorbent Polymer Particles)

The absorber 56 may partially or entirely contain super absorbent polymer particles. Super absorbent polymer particles include "powder" in addition to "particles." The super absorbent polymer particles 54 may be those used in similar types of disposable diapers. Preferred examples of such particles include particles of 30 weight % or less remaining on a standard 500-μm sieve (JIS Z8801-1:2006) after sifting (shook for five minutes) or particles of 60 weight % or more remaining on a standard 180-μm sieve (JIS Z8801-1:2006) after sifting (shook for five minutes).

Any material for the super absorbent polymer particles can be used without any limitation. Preferably, the material has water absorption capacity of 40 g/g or more. Examples of the super absorbent polymer particles are based on starch, cellulose, and synthetic polymer, such as graft copolymer of starch and acrylic acid (salt), saponified copolymers of starch and polyacrylonitrile, cross-linked sodium carboxymethyl cellulose, and acrylic acid (salt) copolymer. Preferably, the super absorbent polymer particles have a generally used particulate form. Alternatively, the super absorbent polymer particles may have another form.

The super absorbent polymer particles have a water absorption rate of 70 second or less, preferably 40 seconds or less. A significantly low water absorption rate causes ready returning of the liquid in the absorber 56 to the outside of the absorber 56.

The basis weight of the super absorbent polymer particles can be appropriately determined in accordance with the required absorption volume of the absorber 56 depending on use. Although the basis weight depends on the use, it may be within the range of 50 to 350 g/m$^2$. A basis weight of polymers of less than 50 g/m$^2$ fails to achieve a sufficient absorption volume. A basis weight of polymers of more than 350 g/m$^2$ saturates the absorption volume.

The density or volume of the super absorbent polymer particles dispersed in the absorber 56 may be adjusted in the planer direction, as required. For example, the volume of the particles at the liquid excretion site may be higher than the volume at the other sites. In consideration of the difference between male and female physiology, the density or volume can be increased in the front portion in diapers for male and the density or volume can be increased in the central portion in diapers for female. Alternatively, sections free from polymers may be provided locally (in spots, for example) in the planar direction of the absorber 56.

(Wrapping Sheet)

Examples of the material for the wrapping sheet 58 include tissue paper, crepe paper, non-woven fabric, polyethylene laminated non-woven fabric, and a porous sheet. Preferably, the super absorbent polymer particles do not pass through the sheet. In the case where non-woven fabric is used in place of crepe paper, hydrophilic SMS (SMS, SSMMS and the like) non-woven fabric is preferred. Examples of such materials include polypropylene and polyethylene/polypropylene composite. The basis weight is within the range of 5 to 40 g/m², preferably 10 to 30 g/m².

The wrapping sheet 58 may have any appropriate configuration. In view of ready production and prevention of leakage of the super absorbent polymer particles from the front-back edges, it is preferred that the wrapping sheet 58 be cylindrically wound around the front and back faces and the two edges of the absorber 56, the front and back edges of the wrapping sheet 58 respectively protrude from the front and back edges of the absorber 56, and the wound portion and the portions protruding in the front-back direction of the wrapping sheet 58 be bonded with a hot-melt adhesive agent or by a bonding means, such as material welding.

(Outer Member)

The front outer member 12F is disposed in the front body F and the back outer member 12B is disposed in the back body B. The front outer member 12F and the back outer member 12B are discontinuous in the crotch region and separated in front-back direction. The distance of separation 12d may be within the range of approximately 150 to 250 mm. It is preferred that a crotch cover sheet 12M composed of non-woven fabric or the like be bonded to the entire of the back face of the inner member 200 or a section of the back face of the inner member 200 exposed through the separation (the section extending in the front-back direction of the exposed inner member 200 between the front outer member 12F and the back outer member 12B without reaching the front-back edges of the inner member 200 and extending in the width direction without reaching both side edges of the inner member 200, for example). Alternatively, the crotch cover sheet 12M may be omitted. Alternatively, the outer members 12 may be an integrated body of the front body F and the back body B through the crotch, as illustrated FIG. 8. That is, the outer members 12F and 12B of the front body F and the back body B, respectively, are separated in the former configuration, whereas the outer members 12 of the front body F and back body B are integrated in the latter configuration.

The outer members 12F and 12B have lower torso portions, respectively, as corresponding ranges in the front-back direction to the lower torso region T. In this embodiment, the front outer member 12F has no portion corresponding to the intermediate region L, whereas the back outer member 12B has a gluteal cover portion 14 extending from the lower torso region T into the intermediate region L. Although not illustrated, the front outer member 12F may also be provided with an inguinal cover portion extending from the waist region T into the intermediate region L; the front outer member 12F may be provided with an inguinal cover portion and without a gluteal cover portion; or both the front outer member 12F and the back outer member 12B may be free from portions corresponding to the intermediate region L. In the illustrated embodiments, the lower edge of the gluteal cover portion 14 is a straight line extending in the width direction, like the lower edge of the front outer member 12F. Alternatively, the lower edge of the gluteal cover portion 14 may be curved such that the outer ends of the lower edge in the width direction are closer to the waist opening.

Figure 7:
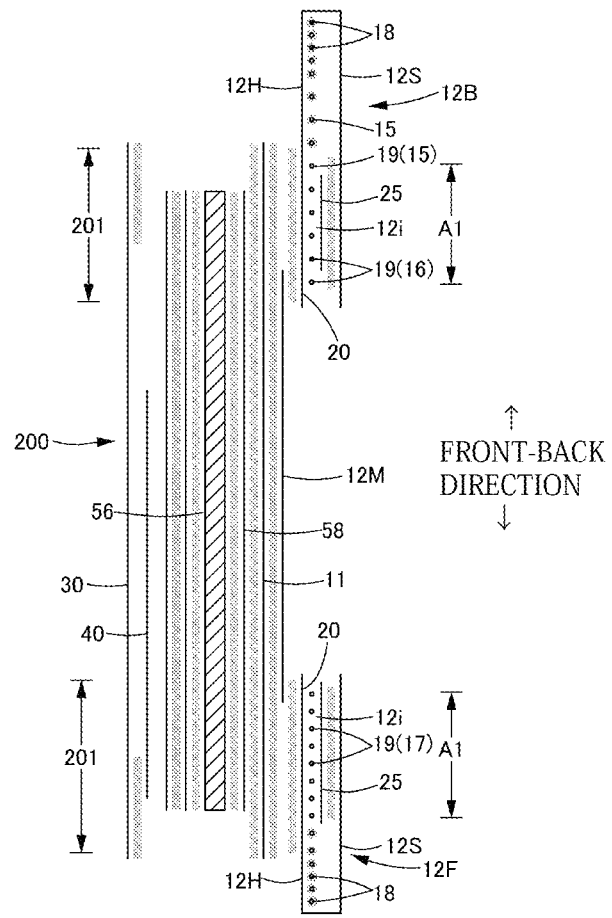
FIG. 7 is a cross-sectional view equivalent to the cross-sectional view taken along line 5-5 in FIG. 1.

The outer members 12F and 12B are each provided with an outer sheet layer 12S and an inner sheet layer 12H bonded with a hot-melt adhesive agent or by a bonding means, such as welding, as illustrated in FIGS. 3 to 5. The sheet material of the outer sheet layer 12S and the sheet material of the inner sheet layer 12H may be composed of separate sheet materials as illustrated in FIG. 5 or may be a single sheet material as illustrated in FIG. 7. In the latter case, the inner face and the outer face of a single sheet material turned back at the edge of the waist opening (or the edge of the crotch) define the inner sheet layer 12H and the outer sheet layer 12S, respectively. The former case is advantageous in that the inner sheet layer 12H and the outer sheet layer 12S are less likely to be misaligned during bonding because of a smaller number of the turn-back steps of the sheet material. The latter case is advantageous in that a smaller number of sheet materials is required.

In the case where the edges of the sheet material(s) of the outer sheet layer 12S and the inner sheet layer 12H and the edges of the inner member 200 in the front-back direction are exposed to the waist opening WO, the corners of the sheet material(s) may come into contact with the skin of the wearer leading to rough feeling and/or the elastic members in the waist region W described below and the hot-melt adhesive agent used for fixing the elastic members may be exposed. Thus, it is preferred that the sheet material of the outer sheet layer 12S be extended and folded over the edge of the sheet material of the inner sheet layer 12H adjacent to the waist opening and the folded portion 12r at the waist opening be extended over the end portion of the inner member 200 adjacent to the waist opening, as illustrated in FIG. 5.

The outer sheet layer 12S and the inner sheet layer 12H may be composed of any sheet material. Preferred examples include thermoplastic resin non-woven fabric composed of synthetic fibers, such as olefin fibers i.e., polyethylene fibers and polypropylene fibers, polyester fibers, and polyamide fibers; and mixed fibers and composite fibers composed of two or more of these fibers. The non-woven fabrics may be produced through any process. Examples of known processes include spunlacing, spunbonding, thermal bonding, melt blowing, needle punching, air through bonding, and point bonding. For use of non-woven fabric, the preferred basis weight is within the range of approximately 10 to 30 g/m².

The preferred total basis weight of the outer members 12F and 12B is within the range of approximately 20 to 60 g/m².

(Stretchable Region)

In the outer members 12F and 12B, elongated elastic members 15 to 18, such as rubber threads, are fixed between the outer sheet layer 12S and the inner sheet layer 12H at a predetermined stretch rate to define a stretchable region A1 that stretches and contracts in the circumferential direction of the lower torso so as to enhance fit to the lower torso of the wearer. The elastic members 15 to 18 may be composed of synthetic rubber or natural rubber.

Figure 8:
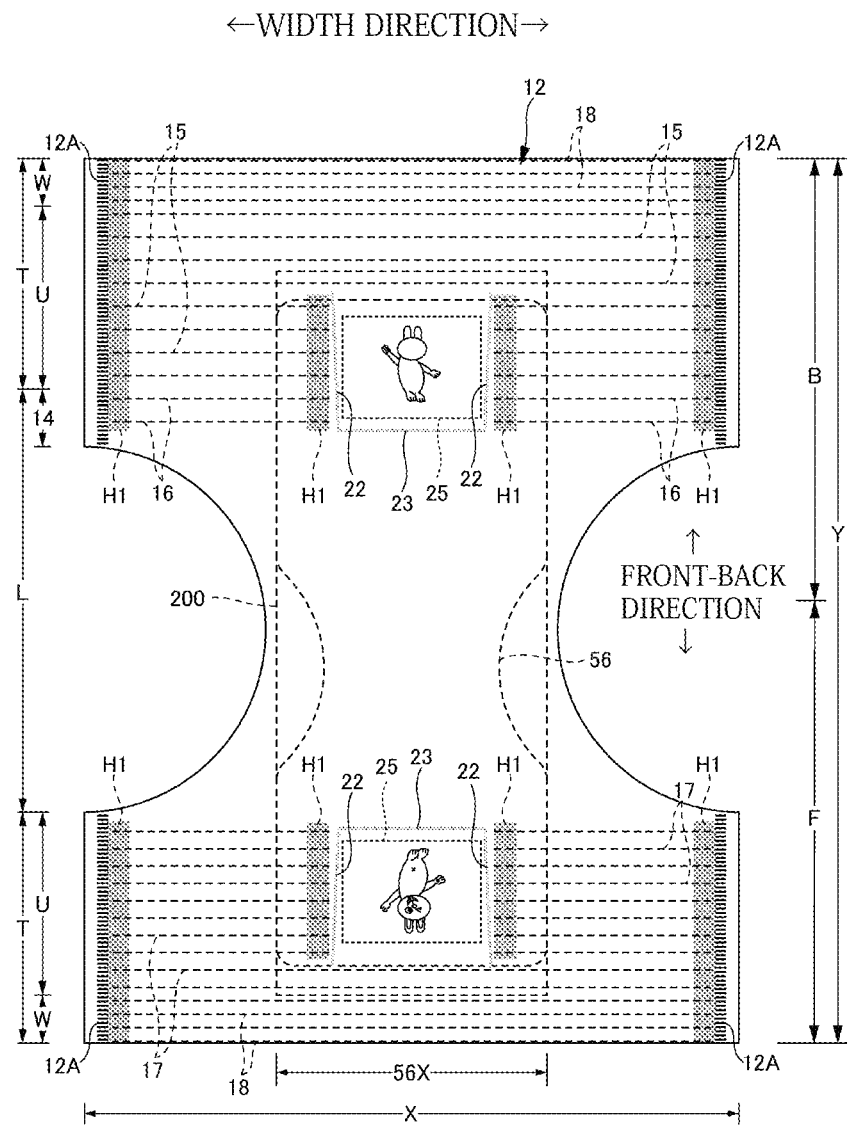
FIG. 8 is a plan view of the outer face of the underpants-type disposable diaper in a spread state.

In the outer members 12F and 12B, the bonding of the outer sheet layer 12S and the inner sheet layer 12H and the fixing of the elongated elastic members 15 to 18 between the inner layer and the outer layer can be achieved with at least one of a hot-melt adhesive agent applied through any means and a fixing means for welding materials, such as heat sealing and ultrasonic sealing. The fixing positions of the elastic members 15 to 18 to the outer sheet layer 12S and the inner sheet layer 12H in the stretchable regions A1 may be appropriately determined so that the stretchable regions A1 contract in the width direction due to the contraction of the elastic members 15 to 18. Thus, the elastic members 15 to 18 should each be fixed at least the two ends in the width direction, for example, fixed along the entire length in the width direction as illustrated in FIG. 2 or fixed only at the two ends in the width direction as illustrated in FIG. 8. In the embodiment illustrated in FIG. 8, the elastic members 15 to 18 are fixed with a hot-melt adhesive agent H1 applied to one of the inner sheet layer 12H and the outer sheet layer 12S through slot application or pattern application (transfer of the hot-melt adhesive agent by relief printing), and the inner sheet layer 12H and the outer sheet layer 12S are bonded together, as required, with a hot-melt adhesive agent or by welding (not shown) at positions other than the positions through which the elastic members 15 to 18 pass. In other embodiments, the hot-melt adhesive agent H1 is applied to only the circumferential faces of the elongated elastic members 15 to 18 by an application tool, such as a comb gun or a Surewrap nozzle, and the elastic members 15 to 18 are disposed between the sheet layers 12S and 12H. The elastic members 15 to 18 are thereby fixed to the sheet layers 12S and 12H and fix the sheet layers 12S and 12H to each other with only the hot-melt adhesive agent H1 applied to the circumferential faces of the elastic members 15 to 18.

The elastic members 15 to 18 may be disposed anywhere as long as the stretchable regions A1 are provided. The illustrated embodiment will now be described in detail below. Multiple waist elastic members 18 are fixed and stretched so as to continuously extend across the entire width between the outer sheet layer 12S and the inner sheet layer 12H in the waist portions W of the outer members 12F and 12B at predetermined intervals in the longitudinal direction at a predetermined stretch rate in the width direction. Among the waist elastic members 18, one or more of the members disposed in the regions adjoining the under-waist portion U may overlap the inner member 200 or may be disposed on the two sides in the width direction, avoiding the intermediate area in the width direction overlapping the inner member 200. Each waist elastic member 18 is preferably composed of approximately 3 to 22 rubber threads having a fineness within the range of approximately 155 to 1880 dtex, specifically 470 to 1240 dtex (synthetic rubber) (for natural rubber, the cross-section is within the range of approximately 0.05 to 1.5 mm$^2$, specifically 0.1 to 1.0 mm$^2$) fixed at intervals within the range of 4 to 12 mm at a stretch rate within the range of approximately 150% to 400%, specifically 220% to 320%. The waist elastic members 18 may have different finenesses and stretch rates. For example, the fineness and stretch rate of the elastic members may differ in the upper and lower areas in the waist portion W.

The under-waist elastic members 15 and 17 composed of elongated elastic members are stretched and fixed so as to extend in the width direction between the outer sheet layer 12S and the inner sheet layer 12H of the under-waist portions U of the outer members 12F and 12B at predetermined intervals in the longitudinal direction and a predetermined stretch rate.

The under-waist elastic members 15 and 17 are approximately 5 to 30 rubber threads each having a fineness within the range of approximately 155 to 1880 dtex, specifically 470 to 1240 dtex (synthetic rubber) (for natural rubber, the cross-section is within the range of approximately 0.05 to 1.5 mm$^2$, specifically 0.1 to 1.0 mm$^2$) fixed at intervals within the range of 1 to 15 mm, specifically 3 to 8 mm at a stretch rate within the range of approximately 200% to 350%, specifically 240% to 300%.

Multiple cover elastic members 16 composed of elongated elastic members are stretched and fixed so as to extend in the width direction between the outer sheet layer 12S and the inner sheet layer 12H of the gluteal cover portion 14 of the back outer sheet 12B at predetermined intervals in the longitudinal direction at a predetermined stretch rate.

Each cover elastic member 16 is preferably composed of approximately two to ten rubber threads having a fineness within the range of approximately 155 to 1880 dtex, specifically 470 to 1240 dtex (synthetic rubber) (for natural rubber, the cross-section is within the range of approximately 0.05 to 1.5 mm$^2$, specifically 0.1 to 1.0 mm$^2$) at intervals within the range of 5 to 40 mm, specifically 5 to 20 mm at a stretch rate within the range of 150% to 300%, specifically 180% to 260%.

In the case where an inguinal cover portion is to be provided on the front outer member 12F, the cover elastic members may be provided in a similar manner.

(Non-Stretchable Region)

In the case where the elastic members 15 to 17 are disposed over a range in the front-back direction containing the absorber 56 in the under-waist portion U and the gluteal cover portion 14, a non-stretchable region A1 is defined as an intermediate region having the entire or part of a portion in the width direction overlapping with the absorber 56 (preferably containing the entire stationary portions 201) in the range in the front-back direction containing the absorber 56 to prevent contraction of the entire or part thereof. Stretchable regions A2 are disposed on two sides of the non-stretchable region A1 to the ends in the width direction.

The non-stretchable region A1 is defined by the inner sheet layer 12H and the outer sheet layer 12S continuing from the stretchable regions A2, a graphic sheet 25 disposed between the inner sheet layer 12H and the outer sheet layer 12S and visible through the outer face, and idle elastic members 19 having at least one of each of residual portions continuing from the elastic members in the stretchable regions A2 and each of cut fragments separated from the elastic members in the two stretchable regions A2. Side portions of the non-stretchable region A1 are defined as no-extra-sheet regions A3 extending outward from the sides of the graphic sheet 25 in the width direction and containing no other sheet between the inner sheet layer 12H and the outer sheet layer 12S.

Figure 14:
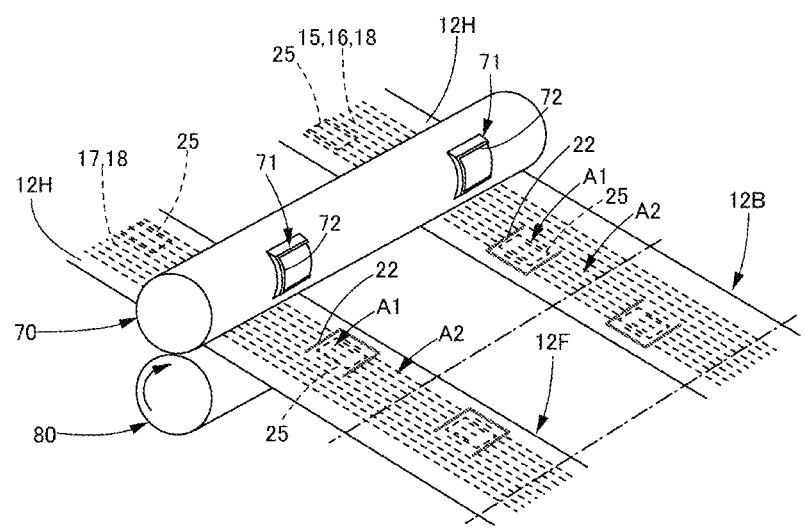
FIG. 14 is a perspective view of a cutting process.

In the process of forming the outer members 12 during the production of the underpants-type disposable diaper, the graphic sheet 25 is disposed between the inner sheet layer 12H and the outer sheet layer 12S in a portion to be the non-stretchable regions A1, and the elongated elastic members 15 to 18 are disposed between the inner sheet layer 12H and the outer sheet layer 12S such that they continuously extend over a portion to be the stretchable region A2, the portion to be the non-stretchable regions A1, a portion overlapping with the graphic sheet 25, and a portion to be the no-extra-sheet region A3, as illustrated in FIG. 14. The elastic members 15 to 18 are fixed to the inner sheet layer 12H and the outer sheet layer 12S with a hot-melt adhesive agent H1 in at least two edge portions of the portions to be the stretchable regions A2 but not fixed to the inner sheet layer 12H and the outer sheet layer 12S in the portion to be the non-stretchable region A1. Then the elastic members 15 to 17 are cut by clamping the inner face of the inner sheet layer 12H and the outer face of the outer sheet layer 12S in the non-stretchable region A1 and applying pressure and heat. The cutting process forms cut marks 22 (pressured or melt marks) in the regions that receive pressure and heat in the product. The elastic members 15 to 18 remaining in the non-stretchable region A1 contract and shift relative to the inner sheet layer 12H and the outer sheet layer 12S. As a result, the elastic member 15 to 18 are converted to idle elastic members 19 that have a natural length or a substantially natural length, and the non-stretchable region A1 is not contracted. In an unfixed state, the elastic members (including idle elastic members) 15 to 19 are shiftable relative to the inner sheet layer 12H and the outer sheet layer 12S (contractable without causing contraction of the inner sheet layer 12H and the outer sheet layer 12S). This may correspond to a state in which the elastic members 15 to 19 are not bonded to the inner sheet layer 12H and the outer sheet layer 12S or a state in which the elastic members 15 to 19 are weakly bonded to the inner sheet layer 12H and the outer sheet layer 12S with a shift-preventing hot-melt adhesive agent H2 and are shiftable relative to the inner sheet layer 12H and the outer sheet layer 12S due to a contracting force.

Although not illustrated, an underpants-type disposable diaper can be produced through the process of forming a continuous structure of the outer members 12F and 12B; sequentially fixing the inner members, which are produced separately, to the outer members; folding the diaper such that the front and back portions overlap; forming side seal portions 12A on the two side edges at the boundaries of adjacent diapers; and cutting the boundaries.

FIG. 14 illustrates the cutting process of the elastic members 15 to 17 in the formation of the outer members 12F and 12B. The cutting process is performed with a seal roll 70 having a circumferential face provided with press members 71 each including a cutting edge 72 having a predetermined cutting pattern and heated to a predetermined temperature; and an anvil roll 80 having a smooth surface and facing the seal roll 70. The targets to be cut, which include the inner sheet layer 12H, the outer sheet layer 12S, and the graphic sheet 25 and the elastic members 15 to 18 disposed between the sheet layers, are disposed between the seal roll 70 and the anvil roll 80 such that the inner sheet layer 12H faces the seal roll (or the anvil roll). Only the elastic members 15 to 17 in the portions nipped between the cutting edges 72 and the circumferential face of the anvil roll 80 are cut by pressure and heat. The temperature of the cutting edges for cutting the elastic members 15 to 17 may be appropriately determined within a temperature that certainly cuts the elastic members 15 to 17. It is preferred that the heating temperature be sufficiently high but lower than the melting point of the elastic members 15 to 17 so that the elastic members 15 to 17 are certainly cut even if the production line operates at a high rate, and the cut portions of the elastic members 15 to 17 do not attach to the neighboring components. For example, the heating temperature may be within the range of 180° C. to 200° C. if the non-woven fabric used for the outer sheet layer 12S and the inner sheet layer 12H has a melting point within the range of approximately 160° C. to 175° C. and the elastic members 15 to 17 have a melting point within the range of approximately 200° C. to 230° C.

More specifically, cutting positions CP are disposed in the no-extra-sheet regions A3 and define a cutting pattern that avoids the cutting of the elastic members 15 to 17 in the portion overlapping with the graphic sheet 25, as illustrated in FIGS. 9 to 13. After the elastic members 15 to 17 are cut in such a cutting pattern, the cut marks 22 are absent in the portion overlapping with the graphic sheet 25 but remain in the no-extra-sheet region A3. In the case where the cutting positions CP of the elastic members 15 to 17 in the non-stretchable region A1 are disposed in the no-extra-sheet regions A3 in which the graphic sheet 25 and other sheets are absent, the thickness of the target to receive pressure, i.e., the pressure applied to the cutting target is uniform in the front-back direction even if the elastic members 15 to 17, which are the cutting targets, are disposed over the corresponding range in the front-back direction to the graphic sheet 25 and at least one of the front side and the back side thereof. Thus, incomplete cutting of the elastic members 15 to 17 will barely occur even if the graphic sheet 25 is disposed between the inner sheet layer 12H and the outer sheet layer 12S in the non-stretchable region A1 of each outer member 12. Since the cut marks 22 do not remain in a region containing the graphic sheet 25, the graphic sheet 25 has a satisfactory appearance.

The no-extra-sheet regions A3 may have any width larger than the width of the cut marks 22 or the width of the cutting edges. In particular, a preferred width is within the range of approximately 3 to 10 mm in consideration of the precision of the cutting positions CP.

Figure 9:
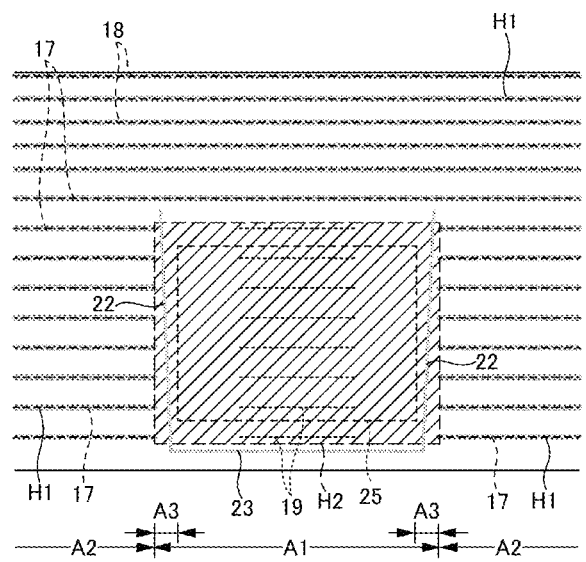
FIG. 9 illustrates a graphic sheet and its neighboring region.
Figure 9B:
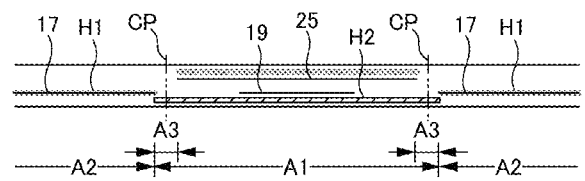
Figure 9C:
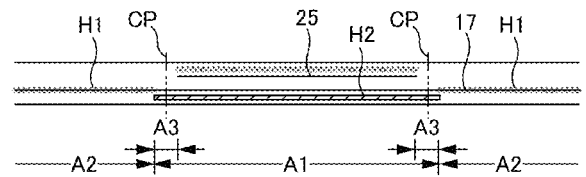
Figure 10:
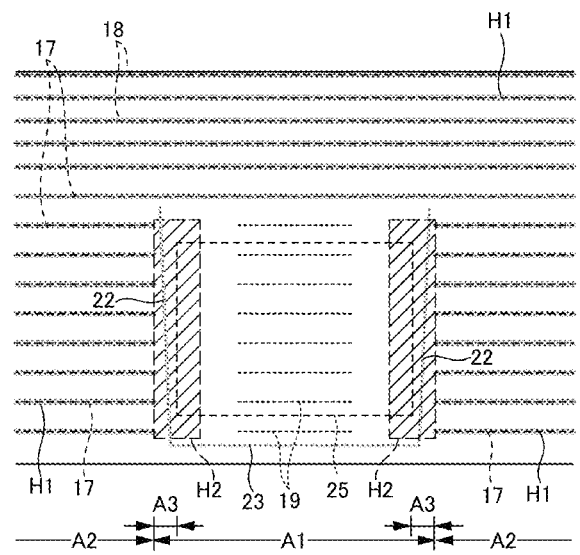
FIG. 10 illustrates a graphic sheet and its neighboring region.
Figure 10:
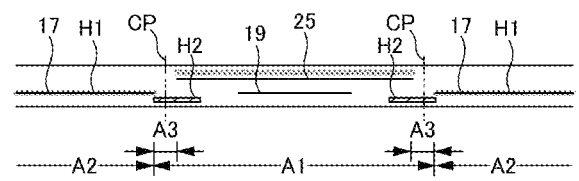
Figure 10:
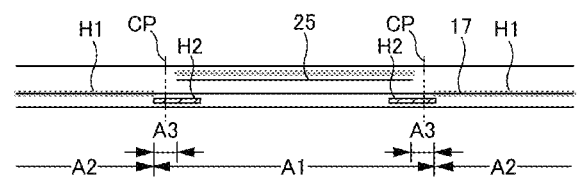
Figure 11:
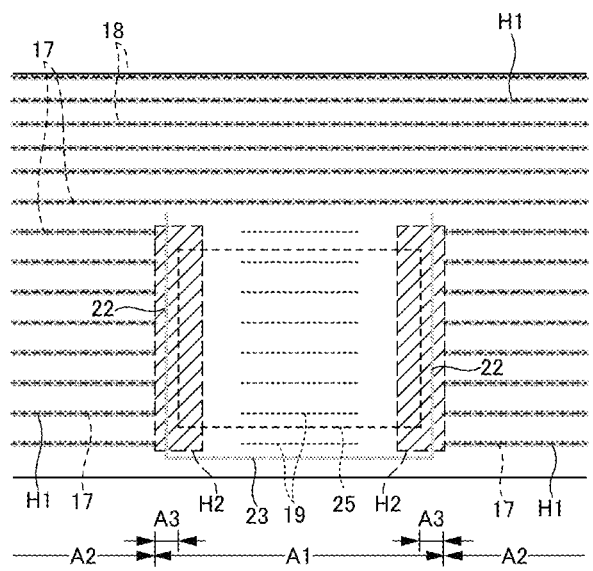
FIG. 11 illustrates a graphic sheet and its neighboring region.
Figure 11:
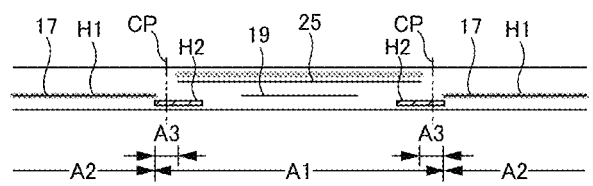
Figure 11:
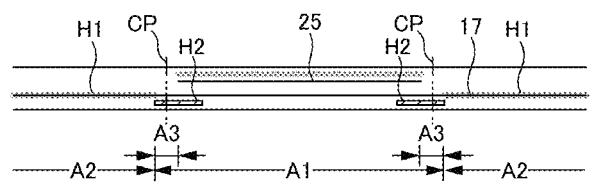
Figure 12:
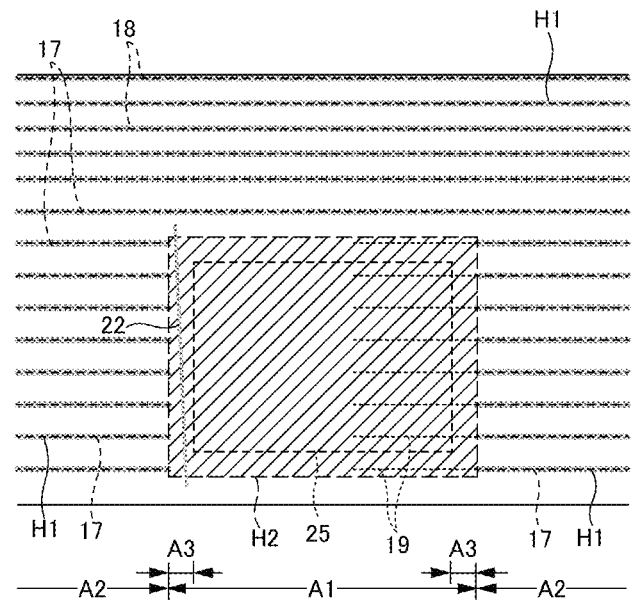
FIG. 12 illustrates a graphic sheet and its neighboring region.
Figure 12:
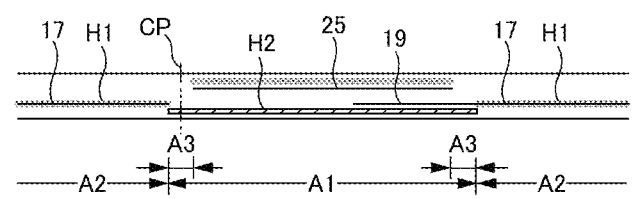
Figure 12:
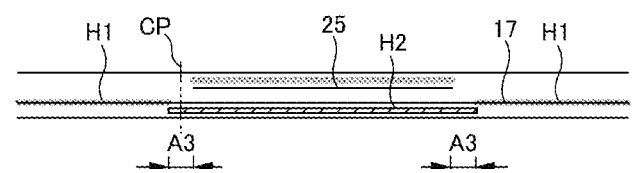
Figure 13:
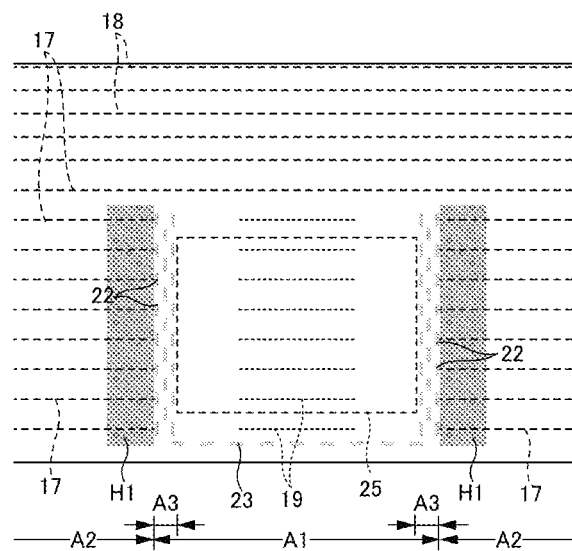
FIG. 13 illustrates a graphic sheet and its neighboring region.
Figure 13:
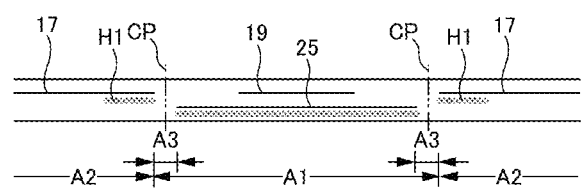
Figure 13:
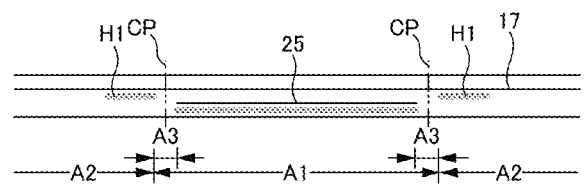

The cutting pattern (cut marks 22) may have any shape, for example, an intermittent pattern in the front-back direction as illustrated in FIG. 13. However, a continuous linear pattern is preferred that at least extends from the cutting position of the elastic members 15 to 17 closest to the waist opening to the cutting position of the elastic members 15 to 17 closest to the crotch on the side edges of the front outer member 12F and the back outer member 12B as illustrated in FIGS. 2, 8, and 9 to 12. Such a linear cutting pattern may include straight lines as illustrated in the drawings. Alternatively, the pattern may include curved lines and wavy lines. The straight lines in such a cutting pattern may be diagonal to the front-back direction; for example, the ends of the straight lines adjacent to the waist opening may tilt outward in the width direction as illustrated in FIGS. 9, 10, and 12 or the straight lines may be parallel to the front-back direction as illustrated in FIG. 11.

The cutting positions CP of the elastic members 15 to 17 may be disposed in the two side portions of the non-stretchable region A1 in the width direction as illustrated in FIGS. 9 to 11 and 13 or may be disposed in only one of the two side portions as illustrated in FIG. 12. In the former configuration, the no-extra-sheet regions A3 should be disposed on the two sides of the graphic sheet 25 in the width direction. In contrast, in the latter configuration, the no-extra-sheet regions A3 may be disposed on the two sides of the graphic sheet 25 in the width direction or on only on the same side as the cutting position CP. In the former configuration, idle elastic members 19 that are not continuous to the elastic members 15 to 17 in the stretchable regions A2 on the two side regions in the width direction remain in the intermediate region of the non-stretchable region A1 in the width direction in a contracted state, as illustrated in the drawings. In the latter configuration, idle elastic members 19 continuous from the elastic members 15 to 17 in the stretchable region A2 opposite to the cut side remain in a contracted state, as illustrated in the drawings.

The elastic members 15 to 17 may shift during cutting as a result of the elastic members 15 to 17 avoiding the pressure being applied. After cutting of the elastic members 15 to 17, the cut ends adjacent to the stretchable regions A2 contract and are pulled toward the stretchable regions A2. This pulling force may cause the elastic members 15 to 17 to be unfixed to the side portions of the stretchable regions A2. With reference to FIGS. 9(c), 10(c), 11(c), 12(c), and 13(c), it is preferred that the elastic members 15 to 17 be fixed to the inner sheet layer 12H and the outer sheet layer 12S with a shift-preventing hot-melt adhesive agent H2 in regions including the cutting positions CP before cutting the elastic members 15 to 17; and then the elastic members 15 to 17 are cut in an intermediate region of the shift-preventing hot-melt adhesive agent H2 in the width direction, as illustrated in FIGS. 9(c), 10(c), 11(c), 12(c), and 13(c), so that the elastic members 15 to 17 contract by their contracting force in a direction against the adhesive force of the shift-preventing hot-melt adhesive agent H2.

The shift-preventing hot-melt adhesive agent H2 may be applied in areas having any width including the cutting positions CP. The hot-melt adhesive agent H2 may be applied to the entire width of the non-stretchable region A1 in the width direction as illustrated in FIGS. 9 and 12 or may be applied only to the two side edges of the non-stretchable region A1 in the width direction as illustrated in FIGS. 10 and 11. The shift-preventing hot-melt adhesive agent H2 may be omitted as illustrated in FIG. 13.

In the case where the front outer member 12F and the back outer member 12B are separately provided in the front-back direction, the gap 12i between the inner sheet layer 12H and the outer sheet layer 12S opens at the edge adjacent to the crotch if the bonding of the inner sheet layer 12H and the outer sheet layer 12S and/or the fixing of the elastic members 15 to 17 to the inner sheet layer 12H and the outer sheet layer 12S are omitted or weakened to enhance flexibility. This causes an unattractive appearance and also the idle elastic members 19 to protrude from or fall out of the opening. In particular, cutting of the elastic members 15 to 17 at the sides of the graphic sheet 25 in the width direction causes the idle elastic members 19 to consist of only cut fragments not continuous from the elastic members 15 to 17 in the stretchable regions A2 on the two sides. Although this emphasizes the boundaries of the stretchable regions A2 and the non-stretchable region A1 and achieves a satisfactory appearance, the idle elastic members 19 readily protrude or fall out of the opening.

With reference to FIGS. 2, 5, 8, 9, 10, 11, and 13, an area on the crotch side of the idle elastic members 19 (on the crotch side of the portion to be the non-stretchable region A1 in producing) may be clamped on the inner face of the inner sheet layer 12H and the outer face of the outer sheet layer 12S, and then the inner sheet layer 12H and the outer sheet layer 12S may be welded by pressure and heat into welded portions 23. Such welded portions 23 completely or partially close the crotch-side opening of the gap 12i between the inner sheet layer 12H and the outer sheet layer 12S. This is preferred because it prevents unattractive appearance and uncomfortable fitting and protrusion or fall out of the idle elastic members 19. The welded portions 23 may be intermittently disposed as illustrated in FIG. 13. However, continuous welded portions 23, as illustrated in FIG. 9, are preferred to certainly achieve the advantages described above.

In a preferred embodiment, the inner face of the inner sheet layer 12H and the outer face of the outer sheet layer 12S are clamped, and pressure and heat are applied to a continuous U-shape from a portion to be one of the no-extra-sheet regions A3 to a portion to be the other no-extra-sheet region A3 through the crotch-side portion of the portion to be the non-stretchable region A1 to cut the elastic members 15 to 17 and weld the inner sheet layer 12H and the outer sheet layer 12S, as illustrated in FIG. 9. Welding in such a U-shaped pattern (the cut marks 22 also have the same shape) not only cuts the elastic members 15 to 17 and welds the area on the crotch side of the idle elastic members 19 at the same time but also a bonded portion surrounding the idle elastic members 19 is formed to effectively prevent protrusion and/or fall out the idle elastic members 19. This also prevents incomplete cutting of the elastic members 15 to 17.

The width of the welded portions 23 can be appropriately determined, for example, within the range of approximately 0.5 to 2.0 mm. The width of the area to receive pressure or to be cut (the width of the cutting edges) may be the same as the width of the welded portions 23.

(Hot-Melt Adhesive Agent)

The fixing hot-melt adhesive agent H1 and the shift-preventing hot-melt adhesive agent H2 of the elastic members may be composed of any material. Examples of such hot-melt adhesive agents include various types of adhesives based on, for example, EVA, adhesive rubber (elastomers), olefins, polyesters, and polyamides. The shift-preventing hot-melt adhesive agent H2 may be composed of a thin layer of the fixing hot-melt adhesive agent H1. However, it is preferred that the shift-preventing hot-melt adhesive agent H2 have a small holding power, for example, within the range of 30 to 90 minutes. In general, the hot-melt adhesive agent H1 having a low melt viscosity has a small holding power. Thus, it is preferred that the shift-preventing hot-melt adhesive agent H2 have a melt viscosity within the range of 3000 to 7000 mpas at 140° C. and 1000 to 4000 mpas at 160° C. A shift-preventing hot-melt adhesive agent H2 satisfying such conditions can be readily available from adhesive agent manufacturers.

(Graphic Sheet)

A graphic sheet 25 having an illustration, for example, of a character is disposed between the outer sheet layer 12S and the inner sheet layer 12H in the non-stretchable region A1 of at least one of the front outer member 12F and the back outer member 12B. The illustration on the graphic sheet 25 can be viewed through the outer sheet layer 12S. The graphic sheet 25 may be disposed adjacent to the inner face of the outer sheet layer 12S (between the outer sheet layer 12S and the idle elastic members 19 described below) as illustrated in FIGS. 9 to 12, or may be disposed adjacent to the outer face of the inner sheet layer 12H (between the inner sheet layer 12H and the idle elastic members 19 described below) as illustrated in FIG. 13.

Any base material may be used for the graphic sheet 25. A preferred example is crepe paper having a thickness within the range of 50 to 200 μm and a density within the range of 50 to 400 km/m$^3$. The thickness of the crepe paper is preferably within the range of 100 to 150μ. The density of the crepe paper is preferably within the range of 100 to 200 kg/m$^3$. Crepe paper having such a thickness and density can be produced with a basis weight of 10 g/m$^2$ or more and a crepe ratio of approximately 10%. The density can be calculated from the basis weight and the thickness. The crepe ratio is expressed by the equation:

(Crepe ratio)=((peripheral velocity of Yankee dryer)−(peripheral velocity of winding reel)/(peripheral velocity of Yankee dryer)×100%

The graphic sheet 25 may have any illustration, such as a decorative pattern (a picture or a spot illustration of a character), use instructions and aids, functional descriptions, such as size, or marks, such as the manufacturer name, the product name, and the characteristic function by means of printing or the like.

It is preferred that the idle elastic members 19 be not fixed to the inner face of the graphic sheet 25 and the outer face of the inner sheet layer 12H to completely eliminate the influence of the contracting force of the idle elastic members 19 applied to the graphic sheet 25. The inner face of the graphic sheet 25, the idle elastic members 19, and the outer face of the inner sheet layer 12H may be unfixed to each other. In detail, the graphic sheet 25 may be fixed to a sheet layer (the inner sheet layer 12H in the illustrated embodiments) having no idle elastic members 19 with a fixing means, such as a hot-melt adhesive agent, whereas the idle elastic members 19 are not fixed to adjacent components (the graphic sheet 25, the inner sheet layer 12H, and the outer sheet layer 12S) (refer to the definition of the term "not fixed" above). In this way, the idle elastic members 19 independently contracts without contraction of the graphic sheet 25. Such a structure can be produced by not applying a hot-melt adhesive agent to regions of the elastic members 15 to 17 disposed in the non-stretchable region A1 so that the elastic members 15 to 17 are not fixed to the inner face of the graphic sheet 25 or the outer face of the inner sheet layer 12H, for example.

However, if the entire graphic sheet 25 is not bonded to the sheet layer adjacent to the idle elastic members 19 (the inner sheet layer 12H in the illustrated embodiments), a continuous gap forms in the interior, thereby the graphic sheet 25 separates from the sheet layer adjacent to the idle elastic members 19. This may lead to unattractive appearance, for example, due to formation of unexpected wrinkles. In contrast, the ship-preventing hot-melt adhesive agent can prevent the formation of such a gap through a boning effect.

<Descriptions of Terms Used in Specification>

The following terms used in the specification should be understood to have the meanings defined below unless otherwise defined in this specification.

"Front-back (longitudinal) direction" refers to the direction connecting the ventral (front) side and the dorsal (back) side, and "width direction" refers to the direction orthogonal to the front-back direction (right-left direction).

"Spread state" refers to a flat spread state without contraction or looseness.

"Stretch rate" refers to a value when a natural length is set to 100%.

"Basis weight" is measured as follows. After preliminary drying of a sample or test piece, the sample or test piece is left in a test room or a test device under normal conditions (an ambient temperature of 20±5° C. and a relative humidity of 65% or less at the testing site) until the weight of the sample or test piece reaches constant mass. Preliminary drying is to achieve the constant mass of the sample or test piece under an environment having a relative humidity within the range of 10% to 25% and a temperature not exceeding 50° C. For fibers having a standard moisture regain of 0.0%, preliminary drying may be omitted. The test piece having constant mass is cut with a cutting template (200×250 mm, ±2 mm) into samples of 200×250 mm (±2 mm). The weight of the sample is measured. The measured weight is multiplied by 20 to determine the weight per square meter, which is defined as the basis weight.

"Thickness" is automatically measured with an automatic thickness gauge (KES-G5 handy compression tester) under a load of 10 gf/cm$^2$ in a pressurized area of 2 cm$^2$.

"Water absorption capacity" is measured in accordance with JIS K7223-1996 standard "Testing method for water absorption capacity of super absorbent polymers"

"Water absorption rate" is defined as "time that elapses before the end point" measured with super absorbent polymers (2 g) and a normal saline solution (50 g) in accordance with JIS K7224-1996 "Testing method for water absorption rate of super absorbent polymers"

Figure 15:
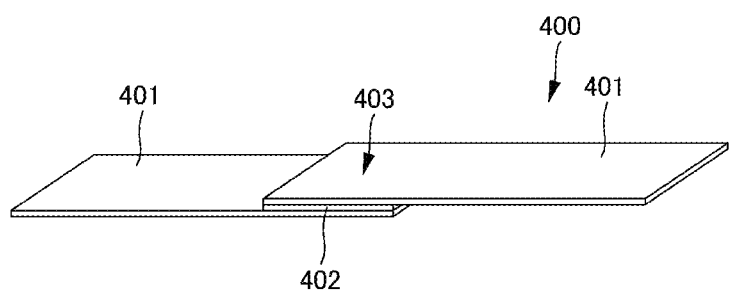
FIG. 15 illustrates a test piece for a holding power measuring test.
Figure 16:
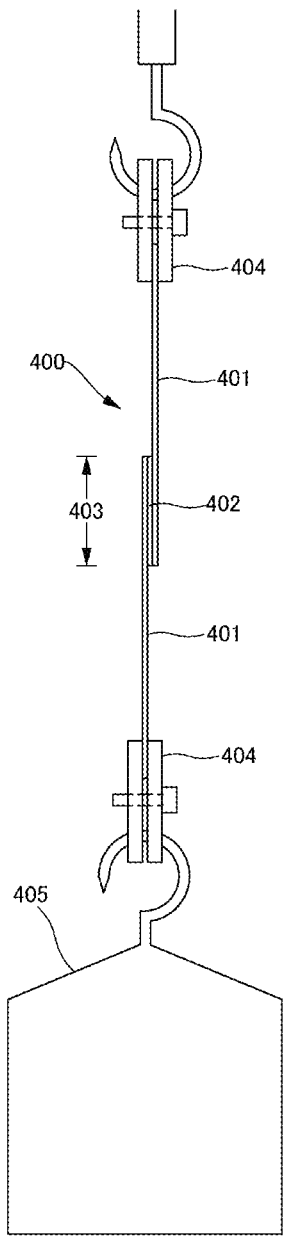
FIG. 16 illustrates the holding power measuring test.

The "holding power" of a hot-melt adhesive agent is measured as follows: A 25-μm-thick PET film is cut into two rectangular PET films 401 that are 100 mm long and 25 mm wide, as illustrated in FIG. 15. The edge portions in the longitudinal directions of the PET films 401 (the area corresponding to 25 mm from one of the edges in the longitudinal direction of each PET film) are bonded with a hot-melt-adhesive-agent layer 402 to be measured, to form a test piece 400. The bonded portion 403 of the test piece 400 is 25×25 mm. The hot-melt-adhesive-agent layer 402 is applied through slot application at a thickness of 20 g/m$^2$. After bonding of the hot-melt-adhesive-agent layer 402, a 2 kg roller is rolled back and forth once over the bonded portion 403 to weld together the films. The test piece 400 is left at room temperature (23° C.) for 16 hours. Then, the two ends of the test fragment or the PET films 401 are clamped with clamps 404 tightened by screws in the thickness direction, as illustrated in FIG. 16. The test piece 400 is then left in a creep tester (thermostatic chamber) at 40° C. for two hours without force applied to the bonded portion 403. Then, the upper one of the clamps 404 is suspended in the creep tester, and a weight 405 is suspended from the lower one of the clamps 404. A vertical load of 1 kg in total (the sum of the weight 405 and the lower clamp 405) is applied to the sample. The time from the start of application of load to the complete separation of the bonded portion 403 or the PET film adjacent to the weight 405 is measured. The time is measured up to 120 minutes. If the weight does not fall before 120 minutes, the measured result is recorded as "above 120 minutes." The time is measured three times, and the average of the measured results is determined to be the holding power (minutes). If the three measurements include one measurement above 120 minutes and two measurements of 120 or less minutes, the average of the two measurements of 120 or less minutes is determined to be the holding power. If two measurements exceed 120 minutes and one measurement is 120 or less minutes, the one measurement of 120 or less minutes is determined to be the holding power. If all three measurements exceed 120 minutes, the holding power is determined to be above 120 minutes.

"Loop tack adhesive strength" is defined as a value measured as described below. In detail, the hot-melt adhesive agent is applied at a thickness of 50 μm on a 50 μm thick PET plate. The PET plate is cut into a strip having a width of 25 mm and a length of 125 mm. Two ends of the strip are overlapped to form a loop. The loop is set in a LT-100 loop tack tester (Cheminstruments Inc.) and then bonded to a polyethylene (PE) plate in a bonding area of 25×25 mm for a bonding time of two seconds. The loop is peeled at a testing speed of 300 mm/min at 20° C. to measure the maximum force as the loop tack adhesive strength.

"Melt viscosity" is measured in accordance with JIS Z 8803 with a Brookfield B-type viscometer (spindle No. 027) at a predetermined temperature.

The tests and measurements are carried out in a laboratory or an apparatus under normal conditions (a temperature of 20±5° C. and a relative humidity of 65% or less at the testing site), unless the environmental condition for the tests and measurements are otherwise specified.

The dimensions of the components are measured in a spread state, not the natural length state, unless otherwise specified.

INDUSTRIAL APPLICABILITY

The present invention is suitable for underpants-type disposable diapers, such as those described above.

REFERENCE SIGNS LIST

A1 non-stretchable region, A2 stretchable region, A3 no-extra-sheet region, H1 hot-melt adhesive agent, H2 shift-preventing hot-melt adhesive agent, L intermediate region, LO leg opening, T lower torso region, U under-waist portion, W waist portion, WO waist opening, 11 liquid impervious sheet, 12 outer member, 12A side seal portion, 12F front outer member, 12B back outer member, 12H inner sheet layer, 12S outer sheet layer, 12$i$ gap, 12$r$ folded portion in waist side, 14 gluteal cover portion, 18 waist elastic member, 19 idle elastic member, 22 cut mark, 23 welded portion, 25 graphic sheet, 30 top sheet, 40 intermediate sheet, 50 absorber element, absorber, 58 wrapping sheet, 60 three-dimensional gather, 62 gather sheet, 200 inner member, 201 stationary portion.

The invention claimed is:

1. An underpants-type disposable diaper comprising:
a front outer member disposed in a front body and a back outer member disposed in a back body, the front outer member and the back outer member comprising a single segment or two discrete segments; and
an inner member disposed from the front outer member to the back outer member, the inner member containing an absorber, wherein,
two side edges of the front outer member and two side edges of the back outer member are bonded together so as to define a waist opening, a left leg opening, and a right leg opening,
at least one of the front outer member and the back outer member has, in a range in the front-back direction containing the absorber, a non-stretchable region at an intermediate position in the width direction and two stretchable regions disposed on two sides of the non-stretchable region in the width direction,
the stretchable region is defined by an inner sheet layer, an outer sheet layer, and elongated elastic members fixed in a stretched state in the width direction at intervals in the front-back direction between the inner sheet layer and the outer sheet layer,
the non-stretchable region is defined by the inner sheet layer and the outer sheet layer continuing from the stretchable region, a graphic sheet disposed between the inner sheet layer and the outer sheet layer and visible through the outer face, and idle elastic members disposed between the inner sheet layer and the outer sheet layer and having at least one of each residual portion continuing from the corresponding elastic member in the stretchable region and each cut fragment separated from the corresponding elastic member in the two stretchable regions, and
the stretchable regions and the non-stretchable region extend over a corresponding range in the front-back direction to the graphic sheet and at least one of the front side and the back side thereof;
wherein at least one no-extra-sheet region is defined by a side portion of the non-stretchable region extending outward from one side of the graphic sheet in the width direction, and the no-extra-sheet region contains no other sheet between the inner sheet layer and the outer sheet layer,
wherein a region coextensive with the graphic sheet has no cut mark of the elastic members; and
wherein the at least one no-extra-sheet region has cut marks of the elastic members.

2. The underpants-type disposable diaper according to claim 1, wherein the cut marks of the elastic members continue in the front-back direction at least from a cutting position of the elastic member closest to the waist opening to a cutting position of the elastic member closest to a crotch.

3. The underpants-type disposable diaper according to claim 2, wherein,
the front outer member is separate from the back outer member in the front-back direction,
the at least one no-extra-sheet region comprises two no-extra-sheet regions disposed on two sides of the graphic sheet in the width direction, and the cut marks are disposed in the no-extra-sheet regions on the two sides of the graphic sheet, and
a welded portion of the inner sheet layer and the outer sheet layer is disposed at an area on the crotch side of the idle elastic members.

4. The underpants-type disposable diaper according to claim 1, wherein,
the front outer member is separate from the back outer member in the front-back direction,
the at least one no-extra-sheet region comprises two no-extra-sheet regions disposed on two sides of the graphic sheet in the width direction, and the cut marks are disposed in the no-extra-sheet regions on the two sides of the graphic sheet, and
a welded portion of the inner sheet layer and the outer sheet layer is disposed at an area on the crotch side of the idle elastic members.

5. An underpants-type disposable diaper comprising:
a front outer member disposed in a front body and a back outer member disposed in a back body, the front outer member and the back outer member comprising a single segment or two discrete segments, wherein the front outer member is separate from the back outer member in the front-back direction; and
an inner member disposed from the front outer member to the back outer member, the inner member containing an absorber, wherein,
two side edges of the front outer member and two side edges of the back outer member are bonded together so as to define a waist opening, a left leg opening, and a right leg opening,
at least one of the front outer member and the back outer member has, in a range in the front-back direction containing the absorber, a non-stretchable region at an intermediate position in the width direction and two stretchable regions disposed on two sides of the non-stretchable region in the width direction,
the stretchable region is defined by an inner sheet layer, an outer sheet layer, and elongated elastic members fixed in a stretched state in the width direction at intervals in the front-back direction between the inner sheet layer and the outer sheet layer,
the non-stretchable region is defined by the inner sheet layer and the outer sheet layer continuing from the stretchable region, a graphic sheet disposed between the inner sheet layer and the outer sheet layer and visible through the outer face, and idle elastic members having at least one of each residual portion continuing from the corresponding elastic member in the stretchable region and each cut fragment separated from the corresponding elastic member in the two stretchable regions, and
the stretchable regions and the non-stretchable region extend over a corresponding range in the front-back direction to the graphic sheet and at least one of the front side and the back side thereof;
wherein two no-extra-sheet regions are defined by side portions of the non-stretchable region extending outward from two sides of the graphic sheet in the width direction, wherein each no-extra-sheet region contains no other sheet between the inner sheet layer and the outer sheet layer,
wherein a region overlapping with the graphic sheet has no cut mark of the elastic members;
wherein the cut marks of the elastic members are disposed in the two no-extra-sheet regions on the two sides of the graphic sheet;

wherein a welded portion of the inner sheet layer and the outer sheet layer is disposed at an area on the crotch side of the idle elastic members; and wherein the inner sheet layer and the outer sheet layer are continuously welded from one of the cut marks to the other cut mark through the welded portion into a U-shape.

6. The underpants-type disposable diaper according to claim 5, wherein the cut marks of the elastic members continue in the front-back direction at least from a cutting position of the elastic member closest to the waist opening to a cutting position of the elastic member closest to a crotch.

7. A method of producing an underpants-type disposable diaper, the underpants-type disposable diaper comprising:
a front outer member disposed in a front body and a back outer member disposed in a back body, the front outer member and the back outer member comprising a single segment or two discrete segments; and
an inner member disposed from the front outer member to the back outer member, the inner member containing an absorber, wherein,
two side edges of the front outer member and two side edges of the back outer member are bonded together so as to define a waist opening, a left leg opening, and a right leg opening,
at least one of the front outer member and the back outer member has, in a range in the front-back direction containing the absorber, a non-stretchable region at an intermediate position in the width direction and two stretchable regions disposed on two sides of the non-stretchable region in the width direction,
the stretchable region is defined by an inner sheet layer, an outer sheet layer, and elongated elastic members fixed in a stretched state in the width direction at intervals in the front-back direction between the inner sheet layer and the outer sheet layer,
the non-stretchable region is defined by the inner sheet layer and the outer sheet layer continuing from the stretchable region, a graphic sheet disposed between the inner sheet layer and the outer sheet layer and visible through the outer face, and idle elastic members having at least one of each residual portion continuing from the corresponding elastic member in the stretchable region and each cut fragment separated from the corresponding elastic member in the two stretchable regions, and
the stretchable regions and the non-stretchable region extend over a corresponding range in the front-back direction to the graphic sheet and at least one of the front side and the back side thereof;
wherein at least one no-extra-sheet region is defined by a side portion of the non-stretchable region extending outward from one side of the graphic sheet in the width direction, and the no-extra-sheet region contains no other sheet between the inner sheet layer and the outer sheet layer, and
wherein a region overlapping with the graphic sheet has no cut mark of the elastic members and the no-extra-sheet region has cut marks of the elastic members;
the method comprising:
forming an outer member by:
disposing the graphic sheet between the inner sheet layer and the outer sheet layer in a portion to be the non-stretchable region;
disposing the elongated elastic members between the inner sheet layer and the outer sheet layer continuously over a portion to be the stretchable region, the portion to be the non-stretchable region, a portion overlapping with the graphic sheet, and a portion to be the at least one no-extra-sheet region;
fixing the elastic members with a hot-melt adhesive agent to the inner sheet layer and the outer sheet layer in at least two edge portions of the portion to be the stretchable regions without fixing the elastic members to the inner sheet layer and the outer sheet layer in the portion to be the non-stretchable region;
subsequently cutting the elastic members extending over the portion to be the no-extra-sheet region by clamping the inner face of the inner sheet layer and the outer face of the outer sheet layer in the portion to be the no-extra-sheet region and applying pressure and heat; and
leaving the elastic members in the region overlapping with the graphic sheet uncut without application of pressure or heat.

8. The method according to claim 7, further comprising:
prior to cutting the elastic members, preventing shift of the elastic members by fixing the elastic members to the inner sheet layer and the outer sheet layer in a region containing a portion to be the cutting positions with a shift-preventing hot-melt adhesive agent; and
subsequently cutting the elastic members in an intermediate region of the shift-preventing hot-melt adhesive agent in the width direction and causing the elastic members to contract against the adhesive force of the shift-preventing hot-melt adhesive agent due to the contracting force of the elastic members.

9. The method according to claim 8, wherein the pressure and heat are applied in a linear pattern continuous in the front-back direction at least from the cutting position of the elastic member closest to the waist opening to the cutting position of the elastic member closest to the crotch.

10. The method according to claim 8, wherein the front outer member is separate from the back outer member in the front-back direction,
the at least one no-extra-sheet region comprises two no-extra-sheet regions disposed on two sides of the graphic sheet in the width direction, and the cut marks are disposed in the no-extra-sheet regions on the two sides of the graphic sheet, and
a welded portion of the inner sheet layer and the outer sheet layer is disposed at an area on the crotch side of the idle elastic members;
the method comprising:
cutting the elastic members by clamping the inner face of the inner sheet layer and the outer face of the outer sheet layer and applying pressure and heat to the corresponding range in the front-back direction to the graphic sheet and at least one of the front side and the back side thereof in portions at the both sides in the width direction to be the two no-extra-sheet regions; and
clamping the inner face of the inner sheet layer and the outer face of the outer sheet layer and applying pressure and heat to the inner and outer sheet layers to weld the inner sheet layer and the outer sheet layer at a crotch-side edge portion of the portion to be the non-stretchable region.

11. The method according to claim 10, further comprising:
clamping the inner face of the inner sheet layer and the outer face of the outer sheet layer and applying pressure and heat to a continuous U-shape from one of portions to be the no-extra-sheet regions to the other portion to be the no-extra-sheet region through a crotch-side portion of the portion to be the non-stretchable region to cut the elastic members and weld the inner sheet layer and the outer sheet layer.

12. The method according to claim 7, wherein the pressure and heat are applied in a linear pattern continuous in the front-back direction at least from the cutting position of the elastic member closest to the waist opening to the cutting position of the elastic member closest to the crotch.

13. The method according to claim 12, wherein the front outer member is separate from the back outer member in the front-back direction,
the at least one no-extra-sheet region comprises two no-extra-sheet regions disposed on two sides of the graphic sheet in the width direction, and the cut marks are disposed in the no-extra-sheet regions on the two sides of the graphic sheet, and
a welded portion of the inner sheet layer and the outer sheet layer is disposed at an area on the crotch side of the idle elastic members;
the method comprising:
cutting the elastic members by clamping the inner face of the inner sheet layer and the outer face of the outer sheet layer and applying pressure and heat to the corresponding range in the front-back direction to the graphic sheet and at least one of the front side and the back side thereof in portions at the both sides in the width direction to be the two no-extra-sheet regions; and
clamping the inner face of the inner sheet layer and the outer face of the outer sheet layer and applying pressure and heat to the inner and outer sheet layers to weld the inner sheet layer and the outer sheet layer at a crotch-side edge portion of the portion to be the non-stretchable region.

14. The method according to claim 13, further comprising:
clamping the inner face of the inner sheet layer and the outer face of the outer sheet layer and applying pressure and heat to a continuous U-shape from one of portions to be the no-extra-sheet regions to the other portion to be the no-extra-sheet region through a crotch-side portion of the portion to be the non-stretchable region to cut the elastic members and weld the inner sheet layer and the outer sheet layer.

15. The method according to claim 9, wherein the front outer member is separate from the back outer member in the front-back direction
the at least one no-extra-sheet region comprises two no-extra-sheet regions disposed on two sides of the graphic sheet in the width direction, and the cut marks are disposed in the no-extra-sheet regions on the two sides of the graphic sheet, and
a welded portion of the inner sheet layer and the outer sheet layer is disposed at an area on the crotch side of the idle elastic members;
the method comprising:
cutting the elastic members by clamping the inner face of the inner sheet layer and the outer face of the outer sheet layer and applying pressure and heat to the corresponding range in the front-back direction to the graphic sheet and at least one of the front side and the back side thereof in portions at the both sides in the width direction to be the two no-extra-sheet regions; and
clamping the inner face of the inner sheet layer and the outer face of the outer sheet layer and applying pressure and heat to the inner and outer sheet layers to weld the inner sheet layer and the outer sheet layer at a crotch-side edge portion of the portion to be the non-stretchable region.

16. The method according to claim 15, further comprising:
clamping the inner face of the inner sheet layer and the outer face of the outer sheet layer and applying pressure and heat to a continuous U-shape from one of portions to be the no-extra-sheet regions to the other portion to be the no-extra-sheet region through a crotch-side portion of the portion to be the non-stretchable region to cut the elastic members and weld the inner sheet layer and the outer sheet layer.

17. The method according to claim 7, wherein the front outer member is separate from the back outer member in the front-back direction,
the at least one no-extra-sheet region comprises two no-extra-sheet regions disposed on two sides of the graphic sheet in the width direction, and the cut marks are disposed in the no-extra-sheet regions on the two sides of the graphic sheet, and
a welded portion of the inner sheet layer and the outer sheet layer is disposed at an area on the crotch side of the idle elastic members;
the method comprising:
cutting the elastic members by clamping the inner face of the inner sheet layer and the outer face of the outer sheet layer and applying pressure and heat to the corresponding range in the front-back direction to the graphic sheet and at least one of the front side and the back side thereof in portions at the both sides in the width direction to be the two no-extra-sheet regions; and
clamping the inner face of the inner sheet layer and the outer face of the outer sheet layer and applying pressure and heat to the inner and outer sheet layers to weld the inner sheet layer and the outer sheet layer at a crotch-side edge portion of the portion to be the non-stretchable region.

18. The method according to claim 17, further comprising:
clamping the inner face of the inner sheet layer and the outer face of the outer sheet layer and applying pressure and heat to a continuous U-shape from one of portions to be the no-extra-sheet regions to the other portion to be the no-extra-sheet region through a crotch-side portion of the portion to be the non-stretchable region to cut the elastic members and weld the inner sheet layer and the outer sheet layer.

\* \* \* \* \*